United States Patent
Hino et al.

(10) Patent No.: US 10,267,762 B2
(45) Date of Patent: Apr. 23, 2019

(54) SENSOR ELEMENT AND GAS SENSOR

(71) Applicant: NGK INSULATORS, LTD., Nagoya-shi, Aichi (JP)

(72) Inventors: Takashi Hino, Nagoya (JP); Mika Murakami, Nagoya (JP); Koichi Masuda, Nagoya (JP); Hironori Sakakibara, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 364 days.

(21) Appl. No.: 15/074,356

(22) Filed: Mar. 18, 2016

(65) Prior Publication Data

US 2016/0282301 A1 Sep. 29, 2016

(30) Foreign Application Priority Data

Mar. 27, 2015 (JP) .................. 2015-066703
Mar. 14, 2016 (JP) .................. 2016-049725

(51) Int. Cl.
*G01N 27/409* (2006.01)
*G01N 27/407* (2006.01)
*G01N 27/41* (2006.01)
*G01N 33/00* (2006.01)

(52) U.S. Cl.
CPC ......... *G01N 27/4077* (2013.01); *G01N 27/41* (2013.01); *G01N 33/0037* (2013.01); *Y02A 50/245* (2018.01)

(58) Field of Classification Search
CPC ........... G01N 27/4067; G01N 27/4077; G01N 27/4078
See application file for complete search history.

(56) References Cited

U.S. PATENT DOCUMENTS

| 5,124,021 A * | 6/1992 | Kaneyasu | ............ G01N 27/417 204/425 |
| 2002/0175077 A1* | 11/2002 | Wahl | ............ G01N 27/419 204/424 |
| 2006/0289314 A1* | 12/2006 | Schnaibel | ............ G01N 27/419 205/782 |

(Continued)

FOREIGN PATENT DOCUMENTS

| CN | 203274779 U * | 11/2013 | ............ G01D 11/24 |
| DE | 102011082173 A1 | 3/2013 | |

(Continued)

OTHER PUBLICATIONS

JPO computer-generated English language translation of Horisaka et al. JP 2011-158390 A. Downloaded Apr. 4, 2018 (Year: 2011).*

(Continued)

*Primary Examiner* — Alexander S Noguerola
(74) *Attorney, Agent, or Firm* — Global IP Counselors, LLP

(57) ABSTRACT

A sensor element includes an element body having an elongate rectangular parallelepiped shape and including solid electrolyte layers with oxygen ion conductivity, an outer pump electrode disposed on a first surface of the element body, and a protective layer covering at least a part of a second surface of the element body on a side opposite to the first surface and including one or more spaces (a lower space) that are present apart from the second surface in a direction perpendicular to the second surface.

17 Claims, 15 Drawing Sheets

(56) References Cited

U.S. PATENT DOCUMENTS

2015/0114102 A1    4/2015  Onkawa et al.

FOREIGN PATENT DOCUMENTS

| JP | 3766572 B2 | 2/2006 | |
|---|---|---|---|
| JP | 20011-158390 A | * 8/2011 | ........... G01N 27/416 |
| JP | 2011-214853 A | 10/2011 | |
| JP | 2012-168030 A | 9/2012 | |

OTHER PUBLICATIONS

EPO computer-generated English language translation of Dang CN 203274779 U . Downloaded Apr. 4, 2018. (Year: 2013).*
EPO computer-generated English language translation of DE 102011082173 A. Downloaded Apr. 5, 2018. (Year: 2013).*
The Extended European Search Report for the corresponding European patent application No. 16161443.3 dated Aug. 8, 2016.

* cited by examiner

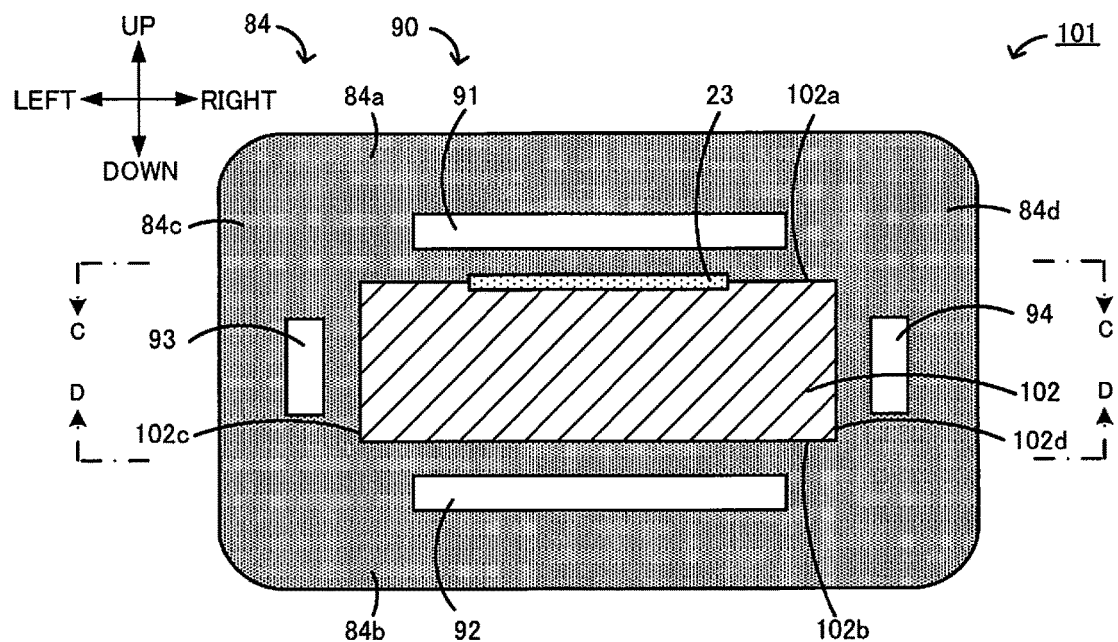
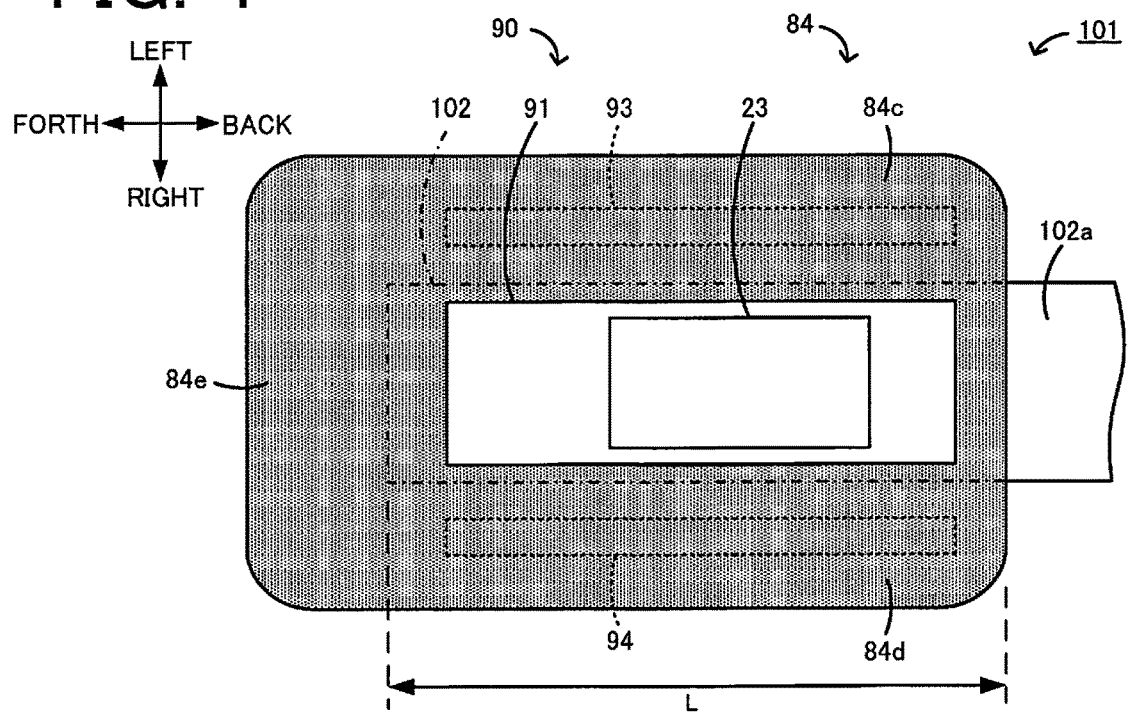

SENSOR ELEMENT AND GAS SENSOR

BACKGROUND OF THE INVENTION

1. Field of the Invention

The present invention relates to a sensor element and a gas sensor.

2. Description of the Related Art

There is so far known a gas sensor including a sensor element that detects the concentration of a specific gas, e.g., NOx, in measurement object gas, such as automobile exhaust gas. It is also known to form a protective layer on a surface of the sensor element in that type of gas sensor. For example, Patent Literatures (PTLs) 1 and 2 disclose that the protective layer is formed on the surface of the sensor element by printing or plasma spraying. According to the disclosures of PTLs 1 and 2, cracking, etc. of the sensor element attributable to adherence of moisture in the measurement object gas, for example, can be suppressed by forming the protective layer.

CITATION LIST

Patent Literature

[PTL 1] JP 2011-214853 A
[PTL 2] JP 3766572 B

SUMMARY OF THE INVENTION

A temperature of the above-mentioned sensor element in the gas sensor is high (e.g., about 800° C.) in an ordinary drive mode. Thus, it is demanded to further suppress cracking of the sensor element, which may occur due to quick cooling with adherence of moisture.

The present invention has been made with intent to solve the Above-described problem, and a main object of the present invention is to improve moisture resistance of an element body of a sensor element.

To achieve the above main object, the present invention is constituted as follows.

A sensor element according to the present invention includes an element body having an elongate rectangular parallelepiped shape and including solid electrolyte layers with oxygen ion conductivity, an outer electrode disposed on a first surface that is one of surfaces of the element body, and a protective layer covering at least a part of a second surface of the element body on a side opposite to the first surface and including one or more spaces that are present apart from the second surface in a direction perpendicular to the second surface.

In the sensor element described above, the protective layer covers at least a part of the second surface on the side opposite to the first surface among the surfaces of the element body on which the outer electrode is disposed. Furthermore, the protective layer includes one or more spaces that are present apart from the second surface in a direction perpendicular to the second surface. With those features, since heat conduction in a direction of thickness of the protective layer can be blocked off by the spaces, cooling of the element body is suppressed when moisture adheres to the surface of the protective layer. Hence the moisture resistance of the element body is improved.

In the sensor element according to the present invention, at least one of the spaces may be positioned in an overlapping relation to the middle of a region of the second surface, the region being covered with the protective layer, when viewed from a direction perpendicular to the second surface. Here, temperature in the middle of the region covered with the protective layer is comparatively more apt to become high, and temperature in a part of the relevant region farther away from the middle (e.g., a part nearer to an end of the second surface) is comparatively less apt to become high. Therefore, the moisture resistance of the element body is further improved by heat-insulating the middle of a region of the second surface, the region being covered with the protective layer, by the space. It is to be noted that the "middle of a region of the second surface, the region being covered with the protective layer" may be the middle of the region covered with the protective layer in a short-length direction of the second surface, or the middle of the relevant region in a longitudinal direction of the second surface, or the middle of the relevant region in each of the short-length direction and the longitudinal direction of the second surface (i.e., the center of the region covered with the protective layer).

In the sensor element according to the present invention, at least one of the spaces may be provided with an opening in communication with the outside of the protective layer. With that feature, since heat in the space can be released through the opening, overheating of the element body is suppressed. As a result, an abrupt temperature drop of the element body can be suppressed when moisture adheres to the surface of the protective layer, and the moisture resistance of the element body is improved.

In the sensor element according to the present invention, the protective layer may include the plurality of spaces, and at least one of the plurality of spaces may be present at a position deviated from at least another one space in the direction perpendicular to the second surface. When those plural spaces are present in the protective layer, strength of the protective layer is less apt to reduce in comparison with the case where the protective layer includes one space having the same total volume as that of the plural spaces. As a result, reduction in the strength of the protective layer attributable to the presence of the spaces can be suppressed while the moisture resistance is improved with the provision of the spaces in the protective layer.

In the sensor element according to the present invention, the protective layer may include, for at least one of the spaces, one or more pillar portions that hold the space in the direction perpendicular to the second surface. With that feature, since the pillar portions hold the space, the reduction in the strength of the protective layer can be suppressed.

In the sensor element of the type including the pillar portions, according to the present invention, the protective layer may include the plurality of pillar portions, and the pillar portions may be arranged with a tendency that a density of the pillar portions gradually increases from the middle of a region of the second surface, the region being covered with the protective layer, toward a position farther away from the middle when viewed from the direction perpendicular to the second surface. Here, temperature in the middle of the region covered with the protective layer is comparatively more apt to become high, and temperature in a part of the relevant region farther away from the middle (e.g., a part nearer to an end of the second surface) is comparatively less apt to become high. Therefore, by arranging the pillar portions at a higher density in a zone where temperature is comparatively less apt to become high, reduction in the heat insulation effect of the space attributable to the presence of the pillar portions can be suppressed in the region where temperature is more apt to become high, while reduction in the strength of the protective layer is suppressed by the pillar portions. It is hence possible to not only further improve the moisture resistance of the element body, but also further suppress the reduction in the strength of the protective layer. The above expression "a tendency that a density of the pillar portions gradually increases" contains a tendency that the number of the pillar portions per unit area gradually increases, and a tendency that thicknesses of the pillar portions gradually increase.

In the sensor element of the type including the pillar portions, according to the present invention, the pillar portions may be arranged with a tendency that a density of the pillar portions gradually increases toward a position nearer to the middle of a region of the second surface, the region being covered with the protective layer, when viewed from the direction perpendicular to the second surface.

In the sensor element according to the present invention, the protective layer may include the plurality of spaces each having a longitudinal direction aligned with the longitudinal direction of the second surface and disposed side by side along the short-length direction of the second surface. With the feature that the plural spaces being elongate in the longitudinal direction of the second surface are present side by side along the short-length direction of the second surface, stress generated, due to a difference in thermal expansion coefficient between the protective layer and the element body when exposed to moisture, in the short-length direction of the second surface and applied from the protective layer to the element body can be reduced. As a result, the element body is less susceptible to cracking when exposed to moisture, and the moisture resistance of the element body is further improved. In this case, the space having a longitudinal direction aligned with the longitudinal direction of the second surface may be a space having a rectangular parallelepiped shape in which one side along the short-length direction of the second surface is shorter than the other two sides.

In the sensor element according to the present invention, the protective layer may include the plurality of spaces each having a longitudinal direction aligned with the short-length direction of the second surface and disposed side by side along the longitudinal direction of the second surface. With the feature that the plural spaces being elongate in the short-length direction of the second surface are present side by side along the longitudinal direction of the second surface, stress generated, due to the difference in thermal expansion coefficient between the protective layer and the element body when exposed to moisture, in the longitudinal direction of the second surface and applied from the protective layer to the element body can be reduced. As a result, the element body is less susceptible to cracking when exposed to moisture, and the moisture resistance of the element body is further improved. In this case, the space having a longitudinal direction aligned with the short-length direction of the second surface may be a space having a rectangular parallelepiped shape in which one side along the longitudinal direction of the second surface is shorter than the other two sides.

In the sensor element according to the present invention, the protective layer may include a plurality of first spaces that are each the space having a longitudinal direction aligned with the longitudinal direction of the second surface, and that are disposed side by side along the short-length direction of the second surface, and a plurality of second spaces that are each the space having a longitudinal direction aligned with the short-length direction of the second surface and intersecting the first spaces, and that are disposed side by side along the longitudinal direction of the second surface. With that feature, stresses generated, due to the difference in thermal expansion coefficient between the protective layer and the element body when exposed to moisture, in the short-length direction and in the longitudinal direction of the second surface and applied from the protective layer to the element body can be both reduced. As a result, the element body is less susceptible to cracking when exposed to moisture, and the moisture resistance of the element body is further improved.

In the sensor element according to the present invention, at least one of the spaces may have a shape with a tendency that the space gradually narrows toward a position farther away from the second surface. With the space having the above-mentioned shape, the reduction in the strength of the protective layer can be suppressed in comparison with, for example, a rectangular parallelepiped space having an inner surface parallel to the second surface.

In the sensor element according to the present invention, at least one of the spaces may have at least two inner surfaces inclined in such directions that the inner surfaces come closer to each other toward a position farther away from the second surface. With the space having the Above-mentioned inner surfaces, the reduction in the strength of the protective layer can be suppressed in comparison with, for example, a rectangular parallelepiped space having an inner surface parallel to the second surface.

In the sensor element according to the present invention, at least one of the spaces may have an inner surface opposing the second surface and formed as a curved surface projecting outward. With the space having the above-mentioned inner surface, the reduction in the strength of the protective layer can be suppressed in comparison with, for example, a rectangular parallelepiped space having an inner surface parallel to the second surface.

A gas sensor according to the present invention includes the above-described sensor element according to any one of the aspects.

The gas sensor includes the above-described sensor element of the present invention according to any one of the aspects. Therefore, an advantageous effect can be obtained which is similar to that obtained with the above-described sensor element of the present invention, e.g., the advantageous effect of improving the moisture resistance of the element body.

BRIEF DESCRIPTION OF THE DRAWINGS

FIG. 3 is a sectional view taken along B-B in FIG. 1.

FIG. 4 is a sectional view taken along C-C in FIG. 3.

DETAILED DESCRIPTION OF THE INVENTION

First Embodiment

Figure 1:
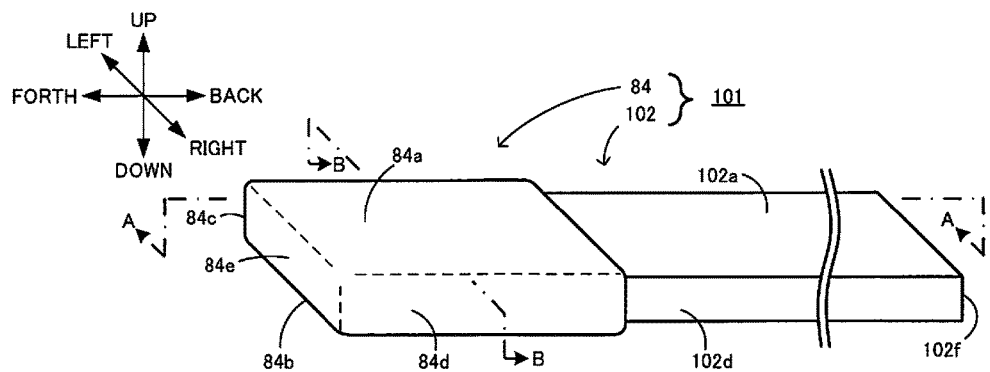
FIG. 1 is a perspective view schematically illustrating one example of constitution of a sensor element 101 according to a first embodiment.
Figure 2:
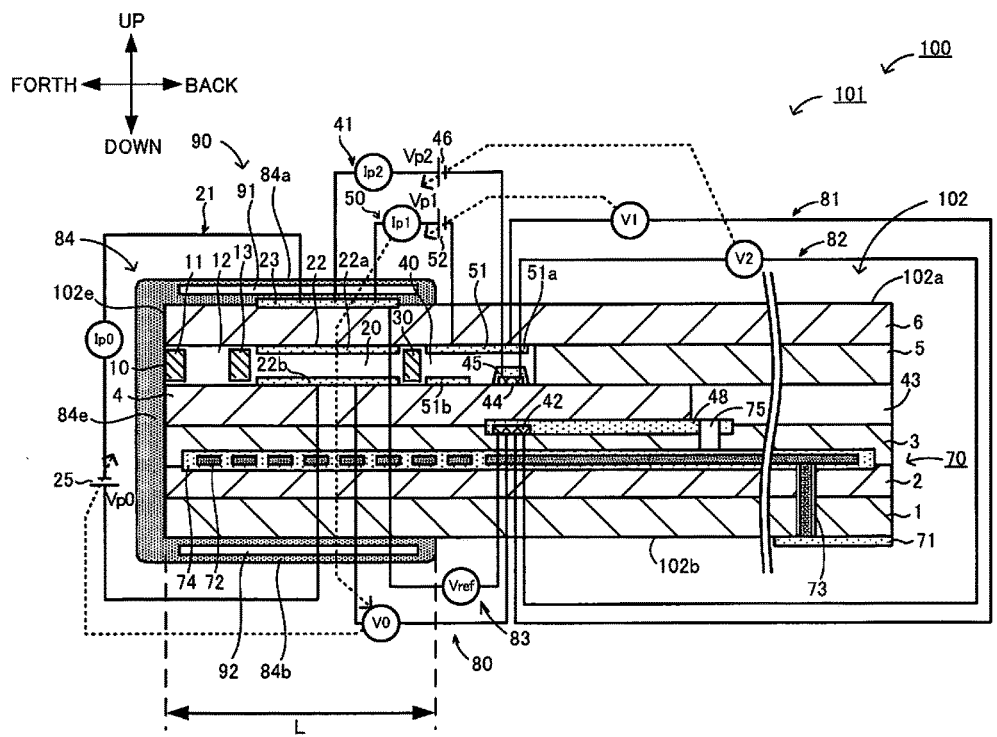
FIG. 2 is a sectional view schematically illustrating one example of constitution of a gas sensor 100 according to a first embodiment.
Figure 5:
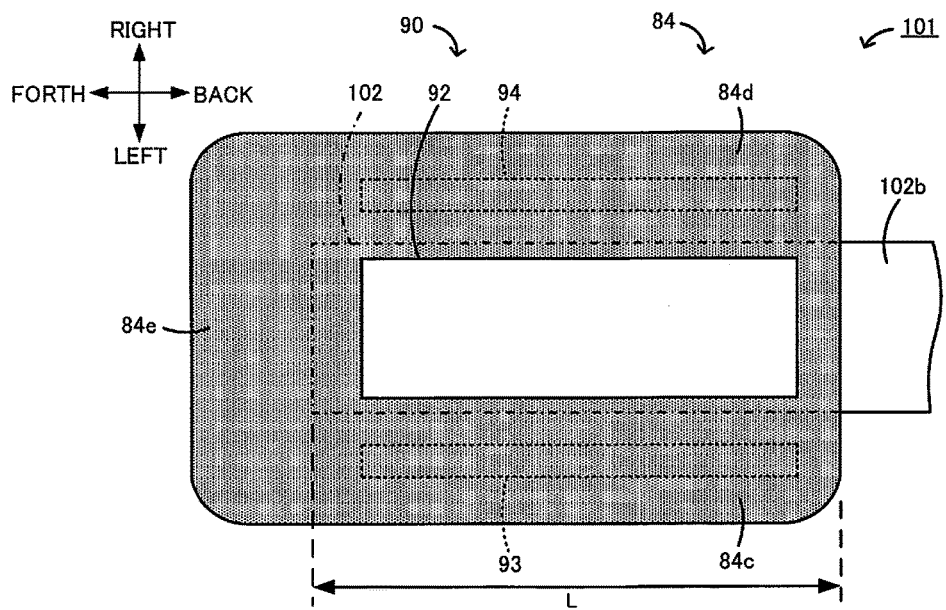
FIG. 5 is a sectional view taken along D-D in FIG. 3.

Embodiments of the present invention will be described below with reference to the drawings. FIG. 1 is a perspective view schematically illustrating one example of constitution of a sensor element 101 included in a gas sensor 100 according to a first embodiment. FIG. 2 is a sectional view schematically illustrating one example of constitution of the gas sensor 100. A section of the sensor element 101 illustrated in FIG. 2 is taken along A-A in FIG. 1. FIG. 3 is a sectional view taken along B-B in FIG. 1. In FIG. 3, details of the inner side in the section of an element body 102 are omitted. FIG. 4 is a sectional view taken along C-C in FIG. 3. FIG. 5 is a sectional view taken along D-D in FIG. 3. The sensor element 101 has an elongate rectangular parallelepiped shape. A longitudinal direction of the sensor element 101 (right-left direction in FIG. 2) is defined as a back-forth direction, and a direction of thickness of the sensor element 101 (up-down direction in FIG. 2) is defined as an up-down direction. Furthermore, a width direction of the sensor element 101 (i.e., a direction perpendicular to both the back-forth direction and the up-down direction) is defined as a right-left direction.

The gas sensor 100 is mounted to a part of piping, e.g., an exhaust gas pipe in a vehicle, and is used to measure the concentration of specific gases, e.g., NOx and $O_2$, contained in exhaust gas that is measurement object gas. In this embodiment, it is assumed that the gas sensor 100 measures the concentration of NOx as one example of the concentration of the specific gas. The gas sensor 100 includes the sensor element 101. The sensor element 101 includes a sensor element body 102, and a porous protective layer 84 covering the sensor element body 102. The sensor element body 102 represents a portion of the sensor element 101 other than the protective layer 84.

As illustrated in FIG. 2, the sensor element 101 is an element having a structure in which six layers, i.e., a first substrate layer 1, a second substrate layer 2, a third substrate layer 3, a first solid electrolyte layer 4, a spacer layer 5, and a second solid electrolyte layer 6, those layers being each made of a solid electrolyte with oxygen ion conductivity, such as zirconia ($ZrO_2$), are successively stacked in the mentioned order from the lower side when viewed in the drawing. The solid electrolyte forming each of those six layers is a dense and air-tight substance. The sensor element 101 is manufactured, for example, by carrying out predetermined processing, printing of a circuit pattern, etc. on ceramic green sheets corresponding to the six layers, respectively, stacking those ceramic green sheets, and then firing the stacked sheets into an integral body.

In one end portion (front end portion) of the sensor element 101 and between a lower surface of the second solid electrolyte layer 6 and an upper surface of the first solid electrolyte layer 4, a gas inlet 10, a first diffusion rate-controlling portion 11, a buffer space 12, a second diffusion rate-controlling portion 13, a first inner cavity 20, a third diffusion rate-controlling portion 30, and a second inner cavity 40 are successively formed adjacent to each other in the mentioned order in a thoroughly communicating state.

The gas inlet 10, the buffer space 12, the first inner cavity 20, and the second inner cavity 40 are each an inner space of the sensor element 101, which is formed by boring the spacer layer 5, and which is defined at its top by the lower surface of the second solid electrolyte layer 6, at its bottom by the upper surface of the first solid electrolyte layer 4, and at its sides by lateral surfaces of the spacer layer 5.

The first diffusion rate-controlling portion 11, the second diffusion rate-controlling portion 13, and the third diffusion rate-controlling portion 30 are each provided as two horizontally-elongate slits (each having an opening with a longitudinal direction thereof being a direction perpendicular to the drawing). A region spanning from the gas inlet 10 to the second inner cavity 40 is also called a gas flowing portion.

At a location farther away from the one end side of the sensor element than the gas flowing portion, a reference gas introducing space 43 is formed between an upper surface of the third substrate layer 3 and a lower surface of the spacer layer 5, and is defined at its sides by lateral surfaces of the first solid electrolyte layer 4. For example, the atmosphere is introduced to the reference gas introducing space 43 as reference gas when the concentration of NOx is measured.

An atmosphere introducing layer 48 is a layer made of porous ceramic. The reference gas is introduced to the atmosphere introducing layer 48 through the reference gas introducing space 43. Furthermore, the atmosphere introducing layer 48 is formed in covering relation to a reference electrode 42.

The reference electrode 42 is an electrode that is formed in a state sandwiched between the upper surface of the third substrate layer 3 and the first solid electrolyte layer 4. As described above, the atmosphere introducing layer 48 in communication with the reference gas introducing space 43 is disposed around the reference electrode 42. As described later, the oxygen concentration (oxygen partial pressure) in each of the first inner cavity 20 and the second inner cavity 40 can be measured with the reference electrode 42.

In the gas flowing portion, the gas inlet 10 provides a region opened to an external space, and the measurement object gas is taken into the sensor element 101 from the external space through the gas inlet 10. The first diffusion rate-controlling portion 11 serves as a region for giving predetermined diffusion resistance to the measurement object gas that has been taken in through the gas inlet 10. The buffer space 12 is a space provided to introduce the measurement Object gas, which has been introduced from the first diffusion rate-controlling portion 11, to the second diffusion rate-controlling portion 13. The second diffusion rate-controlling portion 13 serves as a region for giving predetermined diffusion resistance to the measurement object gas that is introduced from the buffer space 12 to the first inner cavity 20. When the measurement object gas is introduced from the outside of the sensor element 101 to the first inner cavity 20, the measurement object gas is abruptly taken into the inside of the sensor element 101 through the gas inlet 10 due to pressure fluctuations of the measurement object gas in the external space (i.e., due to pulsation of exhaust pressure when the measurement Object gas is exhaust gas of an automobile). At that time, the taken-in measurement object gas is not directly introduced to the first inner cavity 20, but it is introduced to the first inner cavity 20 after fluctuations in the concentration of the measurement object gas have been settled through the first diffusion rate-controlling portion 11, the buffer space 12, and the second diffusion rate-controlling portion 13. As a result, the fluctuations in the concentration of the measurement object gas introduced to the first inner cavity 20 are reduced to a substantially negligible level. The first inner cavity 20 is provided as a space for adjusting the partial pressure of oxygen in the measurement object gas that has been introduced through the second diffusion rate-controlling portion 13. The oxygen partial pressure is adjusted with operation of a main pump cell 21.

The main pump cell 21 is an electrochemical pump cell constituted by an inner pump electrode 22 having a ceiling electrode portion 22a that is disposed on the lower surface of the second solid electrolyte layer 6 in a substantially entire region facing the first inner cavity 20, an outer pump electrode 23 disposed in a state exposed to the external space on an upper surface of the second solid electrolyte layer 6 in a region corresponding to the ceiling electrode portion 22a, and the second solid electrolyte layer 6 sandwiched between those two electrodes.

The inner pump electrode 22 is arranged to extend over respective portions of the solid electrolyte layers on the upper and lower sides (i.e., the second solid electrolyte layer 6 and the first solid electrolyte layer 4), those portions defining the first inner cavity 20, and over portions of the spacer layer 5, which portions define both sidewalls of the first inner cavity 20. More specifically, the ceiling electrode portion 22a is formed on the lower surface of the second solid electrolyte layer 6 in a region providing a ceiling surface of the first inner cavity 20, and a bottom electrode portion 22b is formed on the upper surface of the first solid electrolyte layer 4 in a region providing a bottom surface of the first inner cavity 20. Furthermore, lateral electrode portions (not illustrated) are formed on sidewall surfaces (inner surfaces) of the spacer layer 5 in regions defining both the right and left sidewalls of the first inner cavity 20, to thereby interconnect the ceiling electrode portion 22a and the bottom electrode portion 22b. Thus, the inner pump electrode 22 is disposed in the form of a tunnel-like structure in a zone where the lateral electrode portions are disposed.

The inner pump electrode 22 and the outer pump electrode 23 are each formed as a porous cermet electrode (e.g., a cermet electrode made of Pt and $ZrO_2$ and containing 1% of Au). The inner pump electrode 22 contacting the measurement object gas is made of a material having a weakened reducing ability with respect to NOx components in the measurement object gas.

In the main pump cell 21, oxygen in the first inner cavity 20 can be pumped out to the external space, or oxygen in the external space can be pumped into the first inner cavity 20 by applying a desired pump voltage vp0 between the inner pump electrode 22 and the outer pump electrode 23, thus causing a pump current 40 to flow in a positive direction or a negative direction between the inner pump electrode 22 and the outer pump electrode 23.

Furthermore, to detect the oxygen concentration (oxygen partial pressure) in an atmosphere inside the first inner cavity 20, an electrochemical sensor cell, i.e., an oxygen partial-pressure detection sensor cell 80 for controlling a main pump, is constituted by the inner pump electrode 22, the second solid electrolyte layer 6, the spacer layer 5, the first solid electrolyte layer 4, the third substrate layer 3, and the reference electrode 42.

The oxygen concentration (oxygen partial pressure) in the first inner cavity 20 can be determined by measuring an electromotive force V0 in the oxygen partial-pressure detection sensor cell 80 for controlling the main pump. Moreover, the pump current Ip0 is controlled by feedback controlling the pump voltage Vp0, which is given from a variable power supply 25, such that the electromotive force V0 is held constant. As a result, the oxygen concentration in the first inner cavity 20 can be held at a predetermined constant value.

The third diffusion rate-controlling portion 30 serves as a region for applying predetermined diffusion resistance to the measurement object gas of which oxygen concentration (oxygen partial pressure) has been controlled in the first inner cavity 20 with the operation of the main pump cell 21, and for introducing the relevant measurement object gas to the second inner cavity 40.

The second inner cavity 40 is provided as a space used to perform treatment regarding measurement of the concentration of nitrogen oxides (NOx) in the measurement object gas that has been introduced through the third diffusion rate-controlling portion 30. The measurement of the NOx concentration is mainly performed with the operation of a measurement pump cell 41 in the second inner cavity 40 after the oxygen concentration has been adjusted by an auxiliary pump cell 50 in the second inner cavity 40.

In the second inner cavity 40, further adjustment of the oxygen partial pressure is performed by the auxiliary pump cell 50 on the measurement object gas that has been introduced to the second inner cavity 40 through the third diffusion rate-controlling portion 30 after the adjustment of the oxygen concentration (oxygen partial pressure) in the first inner cavity 20. As a result, the oxygen concentration in the second inner cavity 40 can be held constant with high accuracy, and the concentration of NOx can be measured with high accuracy by the gas sensor 100 of this embodiment.

The auxiliary pump cell 50 is an auxiliary electrochemical pump cell constituted by an auxiliary pump electrode 51 having a ceiling electrode portion 51a, which is disposed on the lower surface, of the second solid electrolyte layer 6 over a substantially entire region facing the second inner cavity 40, the outer pump electrode 23 (note that a suitable electrode outside the sensor element 101 can be used without being limited to the outer pump electrode 23), and the second solid electrolyte layer 6.

The auxiliary pump electrode 51 is disposed inside the second inner cavity 40 in the form of a tunnel-like structure, which is similar to that of the above-mentioned inner pump electrode 22 disposed inside the first inner cavity 20. More specifically, the ceiling electrode portion 51*a* is formed in a region of the second solid electrolyte layer 6, the region providing a ceiling surface of the second inner cavity 40, and a bottom electrode portion 51*b* is formed in a region of the first solid electrolyte layer 4, the region providing a bottom surface of the second inner cavity 40. Furthermore, lateral electrode portions (not illustrated) interconnecting the ceiling electrode portion 51*a* and the bottom electrode portion 51*b* are formed respectively on the right and left wall surfaces of the spacer layer 5 in regions defining sidewalls of the second inner cavity 40. Thus, the auxiliary punt electrode 51 has the tunnel-like structure. Similarly to the inner pump electrode 22, the auxiliary pump electrode 51 is also made of a material having a weakened reducing ability with respect to the NOx components in the measurement object gas.

In the auxiliary pump cell 50, oxygen in an atmosphere inside the second inner cavity 40 can be pumped out to the external space, or oxygen can be pumped into the second inner cavity 40 from the external space by applying a desired voltage Vp1 between the auxiliary pump electrode 51 and the outer pump electrode 23.

Furthermore, to control the oxygen partial pressure in the atmosphere inside the second inner cavity 40, an electrochemical sensor cell, i.e., an oxygen partial-pressure detection sensor cell 81 for controlling an auxiliary pump, is constituted by the auxiliary pump electrode 51, the reference electrode 42, the second solid electrolyte layer 6, the spacer layer 5, the first solid electrolyte layer 4, and the third substrate layer 3.

The auxiliary pump cell 50 performs pumping with the aid of a variable power supply 52 of which voltage is controlled in accordance with an electromotive force V1 that is detected by the oxygen partial-pressure detection sensor cell 81 for controlling the auxiliary pump. As a result, the oxygen partial pressure in the atmosphere inside the second inner cavity 40 can be controlled to a low pressure level at which the measurement of NOx is substantially not affected.

In addition, a pump current Ip1 from the variable power supply 52 is used to control the electromotive force of the oxygen partial-pressure detection sensor cell 80 for controlling the main pump. More specifically, the pump current Ip1 is input as a control signal to the oxygen partial-pressure detection sensor cell 80 for controlling the main pump, in order to control the electromotive force V0 thereof. As a result, a gradient of the oxygen partial pressure in the measurement object gas introduced from the third diffusion rate-controlling portion 30 to the second inner cavity 40 is controlled to be always held constant. When the sensor element is used as a NOx sensor, the oxygen concentration in the second inner cavity 40 is held at a constant value of about 0.001 ppm with the operations of the main pump cell 21 and the auxiliary pump cell 50.

The measurement pump cell 41 measures, inside the second inner cavity 40, the concentration of NOx in the measurement object gas. The measurement pump cell 41 is an electrochemical pump cell that is constituted by a measurement electrode 44 disposed on the upper surface of the first solid electrolyte layer 4 in a region facing the second inner cavity 40 at a position spaced from the third diffusion rate-controlling portion 30, the outer pump electrode 23, the second solid electrolyte layer 6, the spacer layer 5, and the first solid electrolyte layer 4.

The measurement electrode 44 is a porous cermet electrode. The measurement electrode 44 functions also as a NOx reducing catalyst for reducing NOx that is present in an atmosphere inside the second inner cavity 40. In addition, the measurement electrode 44 is covered with a fourth diffusion rate-controlling portion 45.

The fourth diffusion rate-controlling portion 45 is a film made of a ceramic porous body. The fourth diffusion rate-controlling portion 45 serves to restrict an amount of NOx flowing to the measurement electrode 44, and it further functions as a protective film for the measurement electrode 44. In the measurement pump cell 41, oxygen generated through decomposition of nitrogen oxides in an atmosphere around the measurement electrode 44 can be pumped out, and an amount of the generated oxygen can be detected as a pump current Ip2.

To detect the oxygen partial pressure around the measurement electrode 44, an electrochemical sensor cell, i.e., an oxygen partial-pressure detection sensor cell 82 for controlling a measurement pump, is constituted by the first solid electrolyte layer 4, the third substrate layer 3, the measurement electrode 44, and the reference electrode 42. A variable power supply 46 is controlled in accordance with an electromotive force V2 that is detected by the oxygen partial-pressure detection sensor cell 82 for controlling the measurement pump.

The measurement object gas introduced to the second inner cavity 40 reaches the measurement electrode 44 through the fourth diffusion rate-controlling portion 45 under the condition of the oxygen partial pressure being controlled. The nitrogen oxides in the measurement object gas around the measurement electrode 44 are reduced ($2NO \rightarrow N_2+O_2$), thereby generating oxygen. The generated oxygen is subjected to pumping by the measurement pump cell 41. At that time, a voltage vp2 of the variable power supply 46 is controlled such that the electromotive force V2 detected by the oxygen partial-pressure detection sensor cell 82 for controlling the measurement pump is held constant. Because the amount of oxygen generated around the measurement electrode 44 is in proportion to the concentration of the nitrogen oxides in the measurement object gas, the concentration of the nitrogen oxides in the measurement object gas is calculated by employing the pump current Ip2 in the measurement pump cell 41.

Moreover, when the measurement electrode 44, the first solid electrolyte layer 4, the third substrate layer 3, and the reference electrode 42 are combined to constitute an electrochemical sensor cell that serves as an oxygen partial pressure detection means, it is possible to detect an electromotive force depending on a difference between an amount of oxygen generated with reduction of the NOx components, which are present in the atmosphere around the measurement electrode 44, and an amount of oxygen contained in open air as a reference. Accordingly, the concentration of the NOx components in the measurement object gas can also be determined from the detected electromotive force.

In addition, an electrochemical sensor cell 83 is constituted by the second solid electrolyte layer 6, the spacer layer 5, the first solid electrolyte layer 4, the third substrate layer 3, the outer pump electrode 23, and the reference electrode 42. The oxygen partial pressure in the measurement object gas outside the gas sensor can be detected from an electromotive force Vref that is obtained by the sensor cell 83.

In the gas sensor 100 constituted as described above, the measurement object gas having the oxygen partial pressure, which is always held at a low constant value (i.e., a value substantially not affecting the measurement of NOx), is applied to the measurement pump cell 41 with the operations of the main pump cell 21 and the auxiliary pump cell 50.

Thus, the concentration of NOx in the measurement object gas can be determined on the basis of the pump current Ip2 that flows upon pumping-out of oxygen by the measurement pump cell 41, the oxygen being generated with reduction of NOx substantially in proportion to the concentration of NOx in the measurement object gas.

In order to increase the oxygen ion conductivity of the solid electrolyte, the sensor element 101 further includes a heater section 70 with a role of temperature adjustment to heat the sensor element 101 and to hold its temperature. The heater section 70 includes a heater connector electrode 71, a heater 72, a through-hole 73, a heater insulating layer 74, and a pressure release hole 75.

The heater connector electrode 71 is an electrode formed in a state contacting a lower surface of the first substrate layer 1. Electric power can be supplied to the heater section 70 from the outside by connecting the heater connector electrode 71 to an external power supply.

The heater 72 is an electrical resistor formed in a state sandwiched between the second substrate layer 2 and the third substrate layer 3 from below and above, respectively. The heater 72 is connected to the heater connector electrode 71 via the through-hole 73. The heater 72 generates heat with supply of electric power from the outside through the heater connector electrode 71, thereby heating the solid electrolytes, which constitute the sensor element 101, and holding temperatures thereof.

Moreover, the heater 72 is embedded in a state extending over an entire region from the first inner cavity 20 to the second inner cavity 40 such that the sensor element 101 can be entirely adjusted to a temperature at which the above-described solid electrolytes are activated.

The heater insulating layer 74 is an insulating layer made of an insulator, such as alumina, and formed on upper and lower surfaces of the heater 72. The heater insulating layer 74 is formed with intent to provide electrical insulation between the second substrate layer 2 and the heater 72 and electrical insulation between the third substrate layer 3 and the heater 72.

The pressure release hole 75 is formed in a state penetrating through the third substrate layer 3 and communicating with the reference gas introducing space 43. The pressure release hole 75 is provided with intent to relieve a rise of inner pressure attributable to a temperature rise within the heater insulating layer 74.

As illustrated in FIGS. 1 and 2, the element body 102 is partly covered with the protective layer 84. Because the sensor element 101 is in the form of a rectangular parallelepiped, it has six surfaces as outer surfaces of the solid electrolyte layers of the sensor element 101, i.e., a first surface 102a (upper surface), a second surface 102b (lower surface), a third surface 102c (left lateral surface), a fourth surface 102d (right lateral surface), a fifth surface 102e (front end surface), and a sixth surface 102f (rear end surface), as illustrated in FIGS. 1 to 3. The protective layer 84 is made of a porous material, and it includes first to fifth protective layers 84a to 84e that are formed respectively on five ones (first to fifth surfaces 102a to 102e) of the six surfaces (first to sixth surfaces 102a to 102f) of the element body 102. The first to fifth protective layers 84a to 84e are collectively called the protective layer 84. Each of the first to fourth protective layers 84a to 84d covers a region of the surface of the element body 102 on which the relevant protective layer is formed, the region spanning through a distance L (see FIG. 2) from the front end surface of the element body 102 rearwards. The first protective layer 84a covers the first surface 102a including its part where the outer pump electrode 23 is formed (see FIGS. 2 and 3). The fifth protective layer 84e covers the gas inlet 10 as well. However, since the fifth protective layer 84e is made of a porous material, the measurement object gas can reach the gas inlet after flowing through the interior of the protective layer 84e. Thus, the protective layer 84 covers a portion of the element body 102 (which portion includes the front end surface of the element body 102 and extends through the distance L from the front end surface), thereby protecting the relevant portion. In other words, the protective layer 84 serves to suppress cracking of the element body 102, which may occur due to adherence of moisture, etc. contained in the measurement object gas, for example. The distance L is determined to fall within a range of (0<distance L<length of the element body 102 in the longitudinal direction) on the bases of a range where the element body 102 is exposed to the measurement object gas in the gas sensor 100, the position of the outer pump electrode 23, and so on.

In this embodiment, as illustrated in FIG. 1, the element body 102 has a length in the back-forth direction, a width in the right-left direction, and a thickness in the up-down direction, which are different from one another and which satisfy a relation of length>width>thickness. Moreover, the distance L is set to a value larger than values of the width and the thickness of the element body 102.

As illustrated in FIGS. 2 to 5, a space 90 is formed at the inner side of the protective layer 84. More specifically, the first protective layer 84a includes an upper space 91, the second protective layer 84b includes a lower space 92, the third protective layer 84c includes a left space 93, and the fourth protective layer 84d includes a right space 94. Those spaces 91 to 94 are collectively called the space 90.

The upper space 91 is a space that is present apart from the first surface 102a in a direction perpendicular to the first surface 102a, and it is formed in a substantially rectangular parallelepiped shape. As illustrated in FIG. 4, the upper space 91 is positioned over a range including the center of a region of the first surface 102a (i.e., a region of the first surface 102a spanning from the front end surface through the distance L), the region being covered with the protective layer 84 (first protective layer 84a), when viewed from a direction perpendicular to the first surface 102a, namely when looked at in a plan view. In other words, the center of a region of the first surface 102a, the region being covered with the protective layer 84 (first protective layer 84a), is positioned just under the upper space 91. Here, the expression "the center of a region of the first surface 102a, the region being covered with the protective layer 84" implies the middle of the relevant region in each of the back-forth direction and the right-left direction. The upper space 91 may be positioned such that at least a part of the upper space 91 overlaps at least a part of the outer pump electrode 23 when viewed from above. In this embodiment, as illustrated in FIG. 4, the upper space 91 is positioned in an overlapping relation to the entire outer pump electrode 23 (namely, including the entire outer pump electrode 23) when viewed from above.

The lower space 92, the left space 93, and the right space 94, respectively, have a similar shape to that of the upper space 91. Positional relations of the lower space 92, the left space 93, and the right space 94 relative to the second surface 102b, the third surface 102c, and the fourth surface 102d, respectively, are similar to that of the upper space 91 relative to the first surface 102a. The upper space 91 and the lower space 92 are formed in shapes and layouts symmetrical in the up-down direction. The left space 93 and the right space 94 are formed in shapes and layouts symmetrical in the right-left direction.

More specifically, the lower space 92 is a space that is present apart from the second surface 102*b* in a direction perpendicular to the second surface 102*b*, and it is formed in a substantially rectangular parallelepiped shape. As illustrated in FIG. 5, the lower space 92 is positioned over a range including the center of a region of the second surface 102*b* (i.e., a region of the second surface 102*b* spanning from the front end surface through the distance L), the region being covered with the protective layer 84 (second protective layer 84*b*), when viewed from a direction perpendicular to the second surface 102*b*, namely when viewed from below. Thus, the center of a region of the second surface 102*b*, the region being covered with the protective layer 84 (second protective layer 84*b*), is positioned just under the lower space 92. It is to be noted that the expression "the center of a region of the second surface 102*b*, the region being covered with the protective layer 84" implies the middle of the relevant region in each of the back-forth direction and the right-left direction.

The left space 93 is a space that is present apart from the third surface 102*b* in a direction perpendicular to the third surface 102*c*, and it is positioned over a range including the center of a region of the third surface 102*c* (i.e., a region of the third surface 102*c* spanning from the front end surface through the distance L), the region being covered with the protective layer 84 (third protective layer 84*c*), when viewed from a direction perpendicular to the third surface 102*c*, namely when viewed from left. The right space 94 is a space that is present apart from the fourth surface 102*c* in a direction perpendicular to the fourth surface 102*d*, and it is positioned over a range including the center of a region of the fourth surface 102*d* (i.e., a region of the fourth surface 102*d* spanning from the front end surface through the distance L), the region being covered with the protective layer 84 (fourth protective layer 84*d*), when viewed from a direction perpendicular to the fourth surface 102*d*, namely when viewed from right.

The protective layer 84 is made of a porous material, such as an alumina porous material, a zirconia porous material, a spinel porous material, a cordierite porous material, a titania porous material, or a magnesia porous material. In this embodiment, the protective layer 84 is made of an alumina porous material. A film thickness of the protective layer 84 is, e.g., 100 to 1000 μm, and a porosity of the protective layer 84 is, e.g., 5% to 85% by volume, though not being particularly limited to those values.

A method of manufacturing the gas sensor 100 thus constituted will be described below. According to the method of manufacturing the gas sensor 100, the element body 102 is first fabricated, and the protective layer 84 is then formed on the element body 102, whereby the sensor element 101 is manufactured.

A method of fabricating the element body 102 is as follows. First, six ceramic green sheets, each not yet fired, are prepared. Patterns for electrodes, insulating layers, resistance heating bodies, etc. are printed on the individual ceramic green sheets corresponding to the first substrate layer 1, the second substrate layer 2, the third substrate layer 3, the first solid electrolyte layer 4, the spacer layer 5, and the second solid electrolyte layer 6, respectively. After forming the various patterns as described above, the green sheets are dried. Thereafter, the dried green sheets are successively stacked to form a laminate. The laminate thus obtained includes the plurality of element bodies 102. The individual element bodies 102 are obtained by cutting the laminate into pieces per size of each element body 102, and by firing the pieces at a predetermined temperature.

A method of forming the protective layer 84 on the element body 102 will be described below. The protective layer 84 can be formed by suitable one of various methods, such as gel casting, screen printing, dipping, and plasma spraying. The space 90 in the protective layer 84 can be formed by employing a melt-disappearing material (e.g., carbon or theobromine) that disappears with burning.

The gel casting is a process of solidifying slurry through a chemical reaction of the slurry itself, thereby obtaining a shaped body. For example, a part of the element body 102 (i.e., its portion to be covered) is positioned in a state exposed to the interior of a shaping mold. The slurry is introduced to flow into a gap between the shaping mold and the element body 102, and is then solidified. The slurry for use in the gel casting process may be a mixture containing raw material powder (e.g., ceramic particles) of the protective layer 84, a sintering aid, an organic solvent, a dispersant, and a gelling agent. The gelling agent is not limited to particular one insofar as it contains at least two kinds of polymerizable organic compounds. For example, the gelling agent contains two kinds of organic compounds capable of developing the urethane reaction. Those two kinds of organic compounds are, e.g., one of isocyanates and one of polyols. In the preparation of the slurry, a slurry precursor is first prepared by adding the raw material powder, the sintering aid, the organic solvent, and the dispersant together at a predetermined ratio, and mixing them for a predetermined time. Immediately before using the slurry, the gelling agent is added to and mixed with the slurry precursor, whereby the slurry is obtained. As an alternative, at least one or two of the isocyanate, the polyol, and a catalyst, which are components of the gelling agent, may be previously added to the slurry precursor, and the remaining component(s) may be then added at the time of preparing the slurry. The slurry obtained after adding the gelling agent to the slurry precursor is preferably introduced to quickly flow into the shaping mold because the chemical reaction (urethane reaction) of the gelling agent starts to progress with the lapse of time.

The protective layer 84 is formed, by way of example, as follows. First, a portion of the protective layer 84 defining a region (also called an inner region) between the space 90 and the element body 102 is formed on the surfaces of the element body 102. The inner region is a region between the element body 102 and each of the upper space 91, the lower space 92, the left space 93, and the right space 94. The inner region may be formed as one region surrounding the element body 102 from the upper, lower, right, and left sides, or may be formed as individual regions separately positioned on the upper, lower, right, and left sides of the element body 102. Then, a melt-disappearing body is formed in shape corresponding to each of the respective shapes of the upper space 91, the lower space 92, the left space 93, and the right space 94 by coating a melt-disappearing material over a surface of the inner region, and by drying the coated melt-disappearing material. The melt-disappearing material can be coated, for example, by screen printing, gravure printing, or ink jet printing. The melt-disappearing body may be formed by repeating the coating and drying steps plural times. Then, the remaining portion of the protective layer 84 (i.e., the portion of the protective layer 84 other than the inner region having been already formed) is formed. The protective layer 84 including the melt-disappearing body in the shape corresponding to the space 90 at the position apart from the element body 102 is thus formed. Thereafter, the melt-disappearing body is eliminated by burning. As a result, a portion occupied by the melt-disappearing body becomes the space 90, and the protective layer 84 including the space 90 therein is formed. In such a manner, the protective layer 84 is formed on the element body 102, and the sensor element 101 is obtained. When the protective layer 84 is formed by the gel casting, the screen printing, or the dipping, the protective layer 84 is Obtained by solidifying and drying the slurry that becomes the protective layer 84, and then firing the slurry. In that case, the firing of the protective layer 84 and the burning of the melt-disappearing body may be performed at the same time. When the protective layer 84 is formed by the plasma spraying, the melt-disappearing body may be burnt to disappear after forming the protective layer 84.

In the case of forming the protective layer 84 including the melt-disappearing body in the shape corresponding to the space 90 (or the protective layer 84 before the firing), the protective layer 84 and the melt-disappearing body may be formed by repeating formation of a part of the protective layer 84 and a part of the melt-disappearing body such that the protective layer 84 is formed in a state successively laminated from the surface(s) of the element body 102 in the direction of thickness thereof. The protective layer 84 may be formed in a manner of forming the first to fifth protective layers 84a to 84e together, or forming the first to fifth protective layers 84a to 84e one by one.

After fabricating the sensor element 101 as described above, the gas sensor 100 is obtained by placing the sensor element 101 into a predetermined housing, and by assembling the sensor element 101 into a body (not illustrated) of the gas sensor 100.

In use of the gas sensor 100 obtained as described above, the measurement object gas in exhaust piping reaches the sensor element 101 and flows into the gas inlet 10 after passing through the protective layer 84. The sensor element 101 then detects the concentration of NOx in the measurement object gas having flowed into the gas inlet 10. At that time, moisture contained in the measurement Object gas may often adhere to surfaces of the protective layer 84. As described above, the temperature of the element body 102 is adjusted by the heater 72 to a temperature (e.g., about 800° C.) at which the solid electrolytes are activated, and upon moisture adhering to the sensor element body 102, the temperature is abruptly lowered, thus causing cracking of the element body 102 in some cases. Here, the protective layer 84 in this embodiment includes the space 90 at the inner side. Therefore, heat conduction in the direction of thickness of the protective layer 84 (i.e., in the direction toward the element body 102 from the outer peripheral surface of the protective layer 84) can be blocked off by the space 90, and cooling of the element body 102 can be suppressed when moisture adheres to the surfaces of the protective layer 84. More specifically, with the presence of the upper space 91, the lower space 92, the left space 93, and the right space 94, cooling of the element body 102 can be suppressed when moisture adheres to upper, lower, left and right surfaces of the protective layer 84. Accordingly, the moisture resistance of the element body 102 is improved in this embodiment.

Correspondence relations between components in this embodiment and components in the present invention are clarified here. The element body 102 in this embodiment corresponds to an element body in the present invention. Furthermore, the outer pump electrode 23 corresponds to an outer electrode, the lower space 92 corresponds to a space, and the protective layer 84 corresponds to a protective layer.

According to the gas sensor 100 of this embodiment described above in detail, the sensor element 101 includes the element body 102 having the elongate rectangular parallelepiped shape and including the solid electrolyte layers with oxygen ion conductivity, the outer pump electrode 23 disposed on the first surface 102a of the element body 102, and the protective layer 84 covering at least a part of the second surface 102b of the element body 102 on the side opposite to the first surface 102a and including one or more spaces (such as the lower space 92) that are present apart from the second surface 102b in a direction perpendicular to the second surface 102b. With those features, since heat conduction in the direction of thickness of the protective layer 84 (particularly heat conduction in the direction upward from the lower surface of the second protective layer 84b) can be blocked off by the lower space 92, cooling of the element body 102 is suppressed when moisture adheres to the surface of the protective layer 84. Hence the moisture resistance of the element body 102 is improved. In this embodiment, as illustrated in FIG. 2, the heater 72 is disposed on the side lower than the middle of the element body 102 in the up-down direction. In other words, the heater 72 is disposed at a position closer to the second surface 102b than to the first surface 102a. Therefore, temperature of the second surface 102b is comparatively more apt to become high. Accordingly, the feature that the protective layer 84 includes the lower space 92 on the side including the second surface 102b is highly meaningful. Moreover, since cooling of the element body 102 can be suppressed with the presence of the upper space 91, the left space 93, and the right space 94 when moisture adheres to the first, third and fourth protective layers 84a, 84c and 84d, the moisture resistance of the element body 102 is further improved.

The lower space 92 is positioned in an overlapping relation to the middle of a region of the second surface 102b, the region being covered with the protective layer 84, when viewed from the direction perpendicular to the second surface 102b. Here, temperature in the middle of the region covered with the protective layer 84 is comparatively more apt to become high, and temperature in a zone farther away from the middle (e.g., a zone nearer to an end of the second surface 102b) is comparatively less apt to become high. Therefore, the moisture resistance of the element body 102 is further improved by heat-insulating the middle of a region of the second surface 102b, the region being covered with the protective layer 84, by the lower space 92.

Second Embodiment

Figure 6:
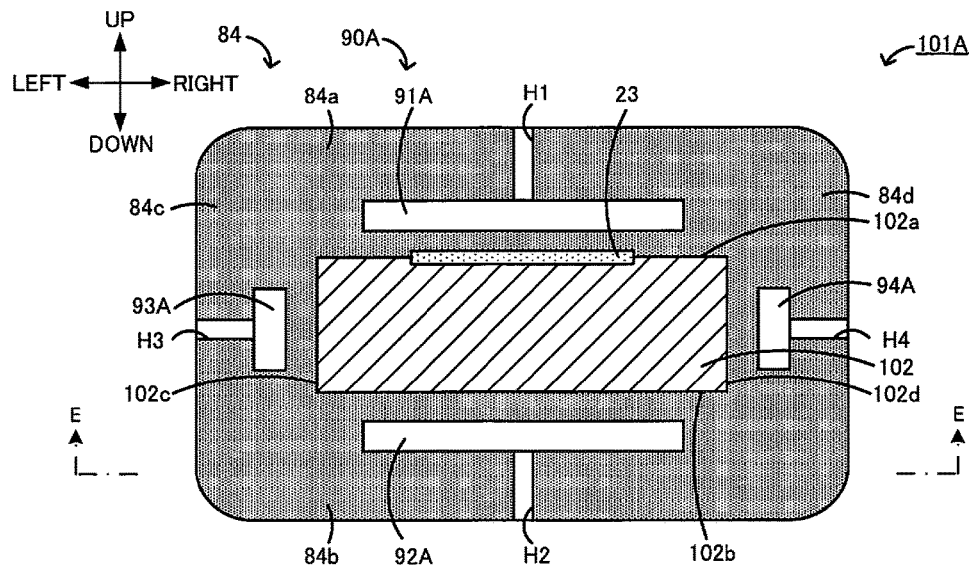
FIG. 6 is a sectional view of a sensor element 101A according to a second embodiment.
Figure 7:
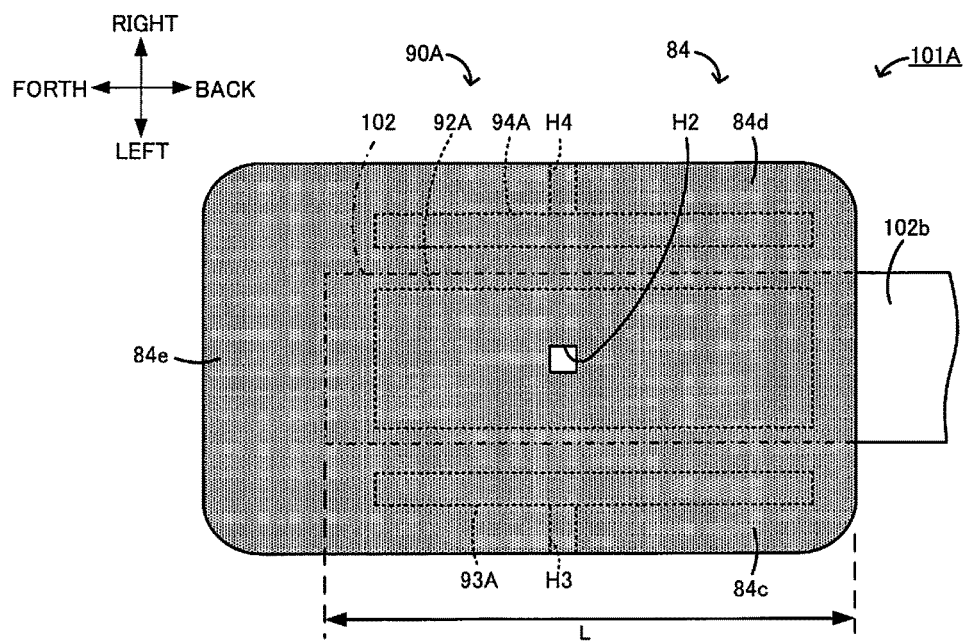
FIG. 7 is a sectional view taken along E-E in FIG. 6.

FIG. 6 is a sectional view of a sensor element 101A according to a second embodiment. FIG. 7 is a sectional view taken along E-E in FIG. 6. The sensor element 101A is similar to the sensor element 101 according to the first embodiment except that the protective layer 84 includes a space 90A different from the space 90.

The space 90A includes an upper space 91A, a lower space 92A, a left space 93A, and a right space 94A. The upper space 91A is similar to the upper space 91 in the first embodiment except for further including a communication hole H1 that is opened to the upper surface of the first protective layer 84a. Likewise, the other spaces 92A to 94A are similar to the spaces 92 to 94 in the first embodiment, respectively, except for further having communication holes H2 to H4 that are opened to the outer surfaces of the protective layer 84.

The communication hole H2 is a rectangular parallelepiped space that is opened in a substantially rectangular shape to the lower surface of the protective layer 84. However, the present invention is not limited to the above case, and the communication hole H2 may be opened in a circular shape, for example. The lower space 92A is communicated with the outside of the protective layer 84 via the communication hole H2. The communication hole H2 may be positioned, when viewed from the direction perpendicular to the second surface 102b, at the middle of a region of the second surface 102b in the back-forth direction, the region being covered with the protective layer 84, at the middle of the relevant region in the right-left direction, or at the center of the relevant region (i.e., at the middle of the relevant region in each of the back-forth direction and the right-left direction).

Positional relations of the communication holes H1, H3 and H4 relative to the corresponding first, third and fourth surfaces 102a, 102c and 102d, respectively, and shapes thereof are similar to the positional relation of the communication hole H2 relative to the second surface 102b and the shape thereof. In this embodiment, the upper space 91A and the lower space 92A are formed in shapes and layouts symmetrical in the up-down direction. The left space 93A and the right space 94A are formed in shapes and layouts symmetrical in the right-left direction.

Also in the sensor element 101A described above, as in the sensor element 101, the moisture resistance of the element body 102 is further improved with the presence of the spaces 91A to 94A. Moreover, the lower space 92A is provided with an opening (opening of the communication hole H2) in communication with the outside of the second protective layer 84b. With the presence of the opening, since heat in the lower space 92A can be released through the opening, overheating of the element body 102 is suppressed. As a result, an abrupt temperature drop of the element body 102 can be suppressed when moisture adheres to the surfaces of the protective layer 84, and the moisture resistance of the element body 102 is improved. Likewise, since the spaces 91A, 93A and 94A are provided with respective openings of the communication holes H1, H3 and H4, the moisture resistance of the element body 102 is improved.

Third Embodiment

Figure 8:
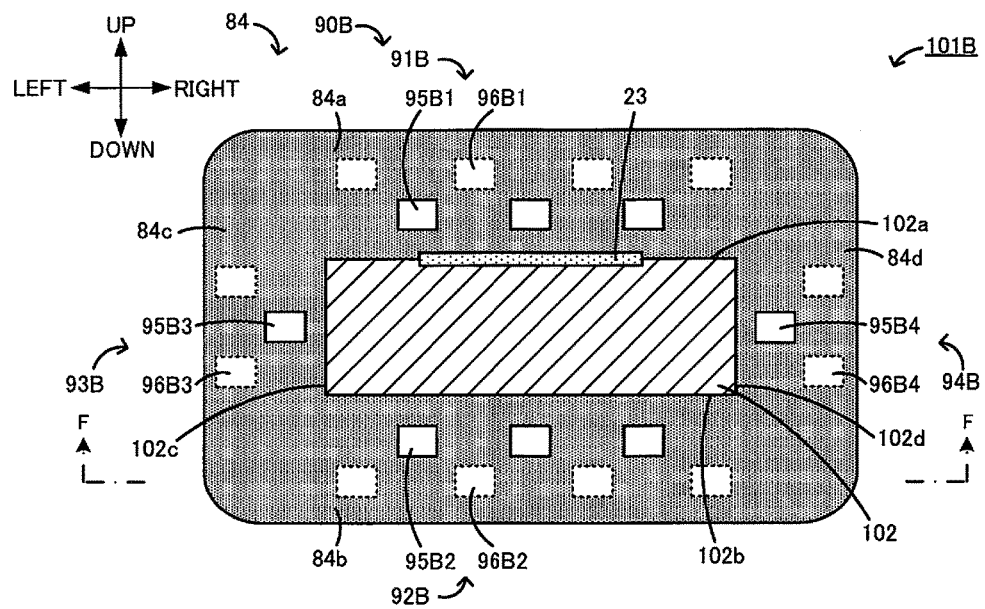
FIG. 8 is a sectional view of a sensor element 101B according to a third embodiment.
Figure 9:
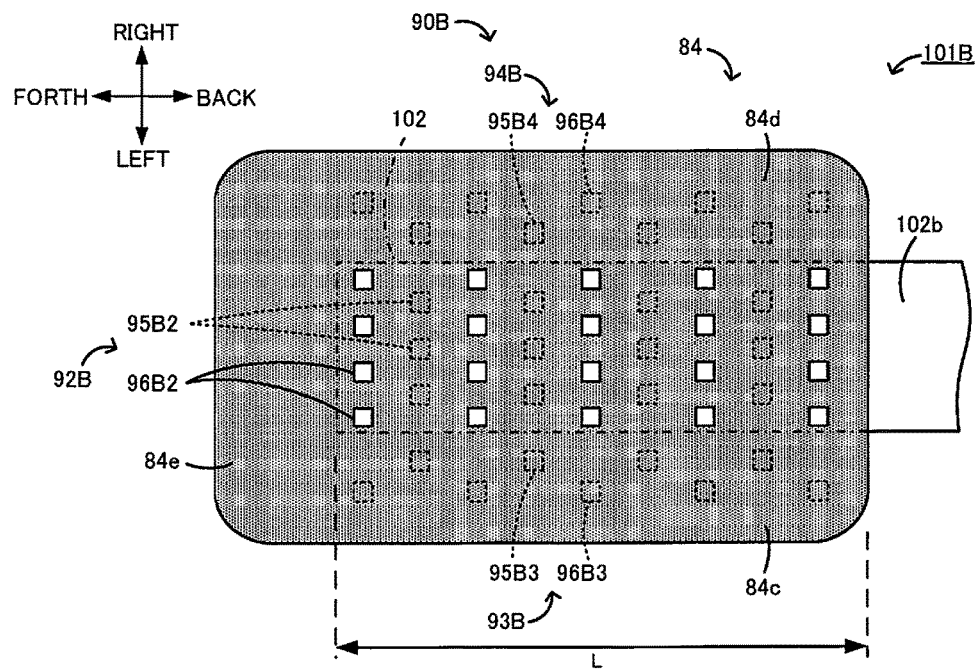
FIG. 9 is a sectional view taken along F-F in FIG. 8.

FIG. 8 is a sectional view of a sensor element 101B according to a third embodiment. FIG. 9 is a sectional view taken along F-F in FIG. 8. The sensor element 101B is similar to the sensor element 101 according to the first embodiment except that the protective layer 84 includes a space 90B different from the space 90.

The space 90B includes an upper space 91B, a lower space 92B, a left space 93B, and a right space 94B. The lower space 92B includes a plurality of inner spaces 95B2 that are present apart from the second surface 102b in the direction perpendicular to the second surface 102b, and a plurality of outer spaces 96B2 that are present at positions deviated from the inner spaces 95B2 in the direction perpendicular to the second surface 102b (downward). The inner spaces 95B2 are each a substantially rectangular parallelepiped space. As illustrated in FIG. 9, there are twelve inner spaces 95B2 in total, namely three in the right-left direction and four in the back-forth direction, which are arrayed in a lattice pattern when viewed from below. The outer spaces 96B2 are each a substantially rectangular parallelepiped space. As illustrated in FIG. 9, there are twenty outer spaces 96B2 in total, namely four in the right-left direction and five in the back-forth direction, which are arrayed in a lattice pattern when viewed from below. All the inner spaces 95B2 have the same length in the up-down direction and are positioned at the same level in the up-down direction. All the outer spaces 96B2 also have the same length in the up-down direction and are positioned at the same level in the up-down direction. Thus, the inner spaces 95B2 and the outer spaces 96B2 are arrayed in two upper and lower stages.

The inner spaces 95B2 and the outer spaces 96B2 are present at different heights in the up-down direction such that their positions do not overlap with each other when viewed from the direction perpendicular to the up-down direction. Furthermore, the inner spaces 95B2 and the outer spaces 96B2 are present at positions deviated from each other in the right-left direction and deviated from each other in the back-forth direction.

The upper space 91B includes a plurality of inner spaces 95B1 that are present apart from the first surface 102a in the direction perpendicular to the first surface 102a, and a plurality of outer spaces 96B1 that are present at positions deviated from the inner spaces 95B1 in the direction perpendicular to the first surface 102a (upward). The left space 93B includes a plurality of inner spaces 95B3 that are present apart from the third surface 102c in the direction perpendicular to the third surface 102c, and a plurality of outer spaces 96B3 that are present at positions deviated from the inner spaces 95B3 in the direction perpendicular to the third surface 102c (leftward). The right space 94B includes a plurality of inner spaces 95B4 that are present apart from the fourth surface 102d in the direction perpendicular to the fourth surface 102d, and a plurality of outer spaces 96B4 that are present at positions deviated from the inner spaces 95B4 in the direction perpendicular to the fourth surface 102d (rightward). Positional relations of the inner spaces 95B1, 95B3 and 95B4 and the outer spaces 96B1, 96B3 and 96B4 relative to the corresponding first, third and fourth surfaces 102a, 102c and 102d, respectively, and shapes thereof are similar to the positional relations of the inner spaces 95B2 and the outer spaces 96B2 relative to the second surface 102b and the shapes thereof. In this embodiment, the inner spaces 95B3 and 95B4 are each formed one in the up-down direction and four in the back-forth direction, i.e., four in total. The outer spaces 96B3 and 96B4 are each formed two in the up-down direction and five in the back-forth direction, i.e., ten in total. Moreover, in this embodiment, the upper space 91B and the lower space 92B are formed in shapes and layouts symmetrical in the up-down direction. The left space 93B and the right space 94B are formed in shapes and layouts symmetrical in the right-left direction.

Also in the sensor element 101B described above, as in the sensor element 101, the moisture resistance of the element body 102 is further improved with the presence of the spaces 91B to 94B. Moreover, the second protective layer 84b includes the plurality of inner spaces 95B2 and the plurality of outer spaces 96B2, and at least one (e.g., the outer space 96B2) of those plural spaces is present at a position deviated from at least another one (e.g., the inner space 95B2) in the direction perpendicular to the second surface 102b. When the plural spaces are present in the second protective layer 84b as described Above, the strength of the second protective layer 84b is less apt to reduce in comparison with the case where one space having the same total volume is present in the second protective layer 84b. Therefore, it is possible to improve the moisture resistance of the element body 102 with the provision of the spaces in the second protective layer 84b, and to suppress the reduction in the strength of the second protective layer 84b, which may occur with the presence of the spaces. Furthermore, since the outer spaces 96B2 are further present at positions deviated from the inner spaces 95B2 in the vertical direction, the positions of the spaces can be more easily arranged farther apart from each other than in the case where the same plural number of spaces having the same shape are all arranged at positions deviated in a direction parallel to the second surface 102b (without being deviated in the vertical direction). As a result, the reduction in the strength of the second protective layer 84b can be further suppressed. With respect to the other spaces 91B, 93B and 94B, similar advantageous effects can be obtained with similar constitutions to that described above.

Fourth Embodiment

Figure 10:
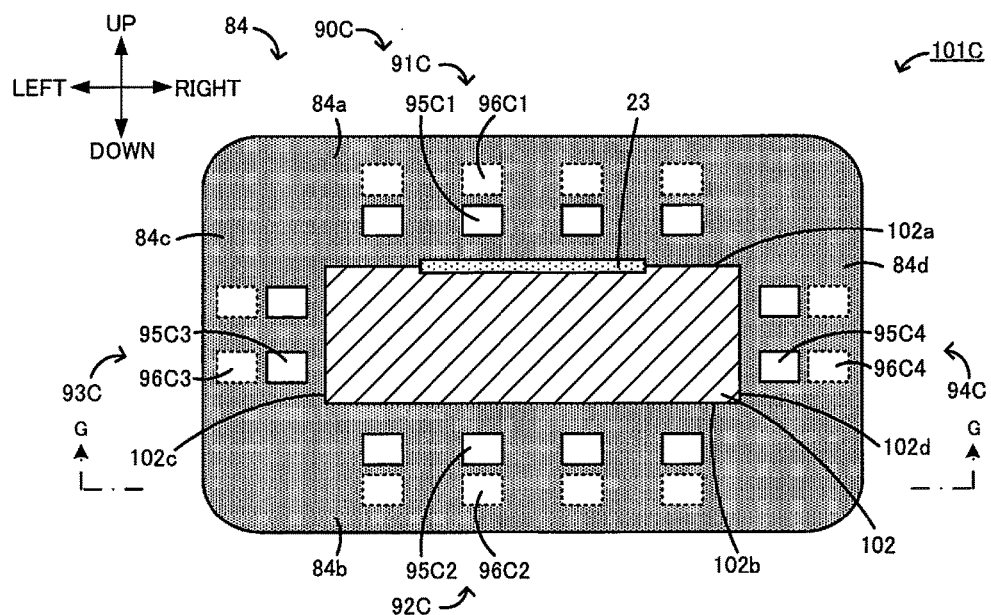
FIG. 10 is a sectional view of a sensor element 101C according to a fourth embodiment.
Figure 11:
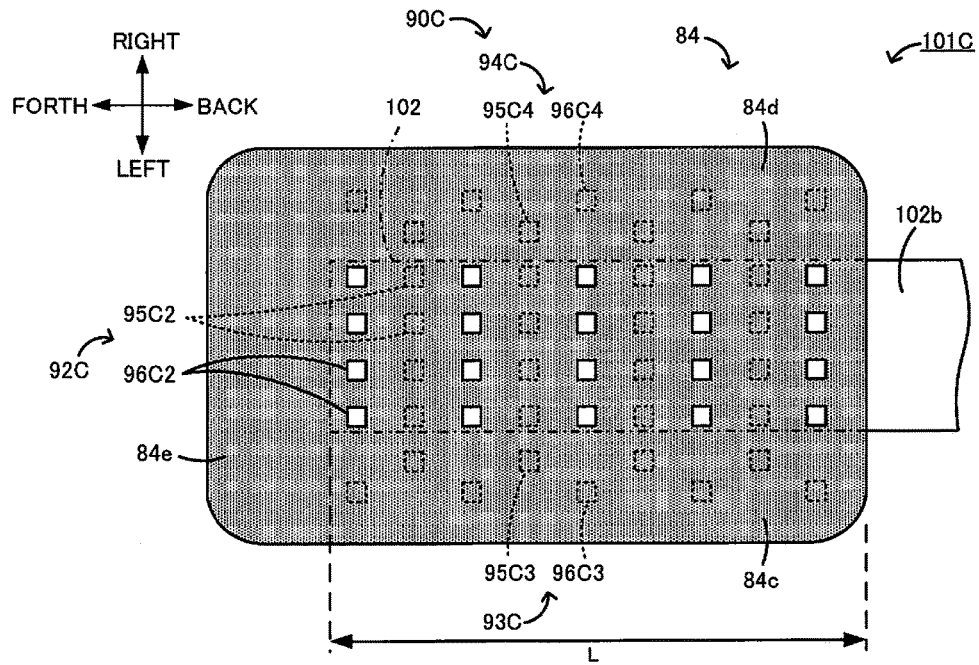
FIG. 11 is a sectional view taken along G-G in FIG. 10.

FIG. 10 is a sectional view of a sensor element 101C according to a fourth embodiment. FIG. 11 is a sectional view taken along G-G in FIG. 10. The sensor element 101C is similar to the sensor element 101B according to the third embodiment except that the protective layer 84 includes a space 90C different from the space 90B.

The space 90C includes an upper space 91C, a lower space 92C, a left space 93C, and a right space 94C. The lower space 92C includes a plurality of inner spaces 95C2 that are present apart from the second surface 102b in the direction perpendicular to the second surface 102b, and a plurality of outer spaces 96C2 that are present at positions deviated from the inner spaces 95C2 in the direction perpendicular to the second surface 102b (downward). Similarly, the spaces 91C, 93C and 94C include plural inner spaces 95C1, 95C3 and 95C4 and plural outer spaces 96C1, 96C3 and 96C4, respectively.

The number, the shape, and the layout of the outer spaces 96C2 are similar to those of the outer spaces 96B2 in the third embodiment. The numbers, the shapes, and the layouts of the outer spaces 96C1, 96C3 and 96C4 are also similar to those of the outer spaces 96B1, 96B3 and 96B4 in the third embodiment, respectively.

The inner spaces 95C2 and the outer spaces 96C2 are present at positions deviated from each other in the direction perpendicular to the second surface 102b and in the back-forth direction, but they are present at the same positions in the right-left direction. This point is different from the positional relation between the inner spaces 95B2 and the outer spaces 96B2 in the third embodiment. As illustrated in FIG. 11, there are sixteen inner spaces 95C2 in total, namely four in the right-left direction and four in the back-forth direction, which are arrayed in a lattice pattern when viewed from below.

Likewise, the other inner spaces 95C1, 95C3 and 95C4 are present at the same positions as the corresponding outer spaces 96C1, 96C3 and 96C4 in the right-left direction, respectively. Positional relations of the inner spaces 95C1, 95C3 and 95C4 relative to the corresponding first, third and fourth surfaces 102a, 102c and 102d, respectively, and shapes thereof are similar to the positional relation of the inner spaces 95C2 relative to the second surface 102b and the shape thereof. In this embodiment, the inner spaces 95C3 and 95C4 are each formed two in the up-down direction and four in the back-forth direction, i.e., eight in total. Furthermore, in this embodiment, the upper space 91C and the lower space 92C are formed in shapes and layouts symmetrical in the up-down direction. The left space 93C and the right space 94C are formed in shapes and layouts symmetrical in the right-left direction.

The sensor element 101C described above can also provide similar advantageous effects to those of the sensor element 101 and the sensor element 101B with similar features.

Fifth Embodiment

Figure 12:
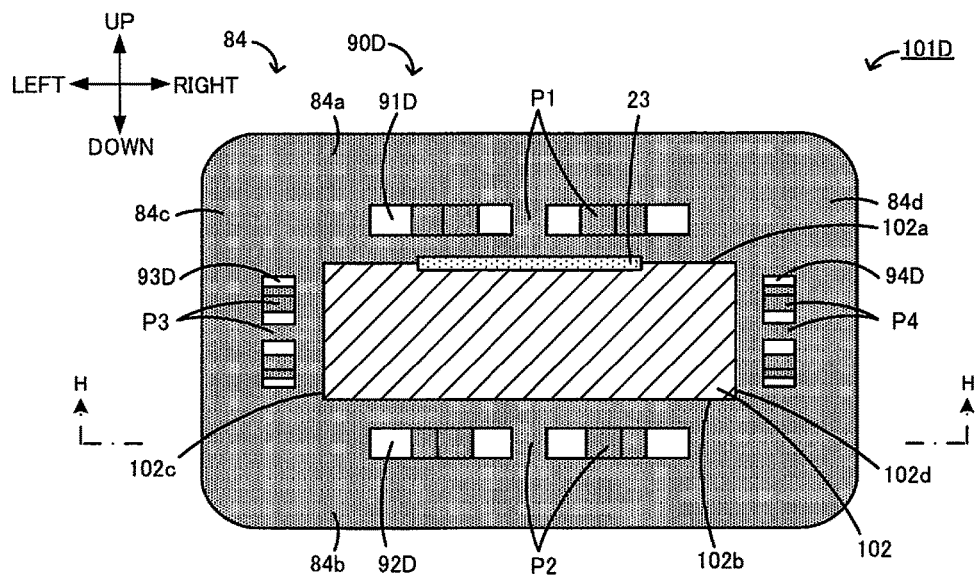
FIG. 12 is a sectional view of a sensor element 101D according to a fifth embodiment.
Figure 13:
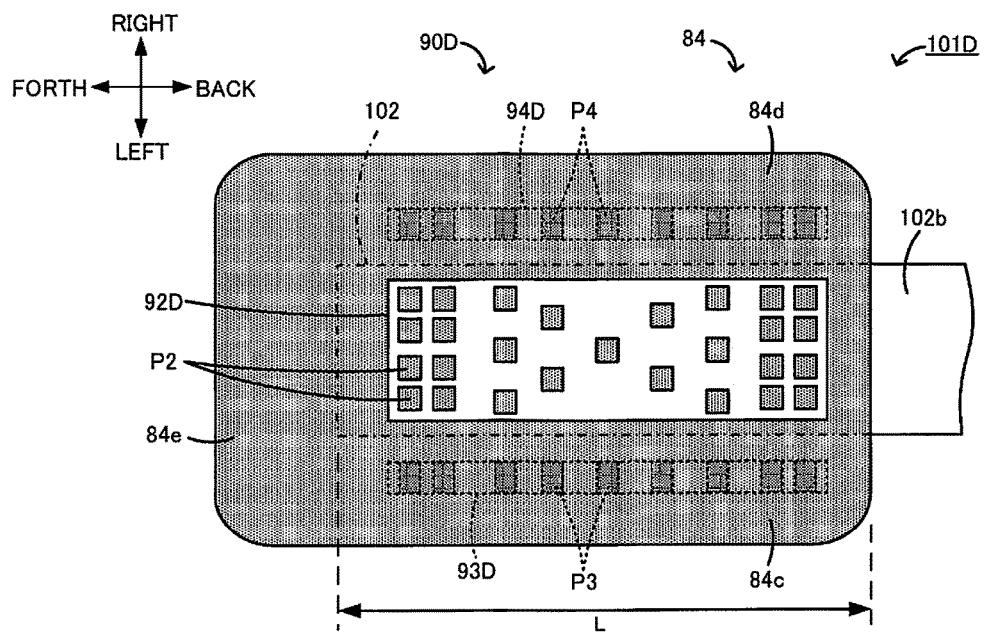
FIG. 13 is a sectional view taken along H-H in FIG. 12.

FIG. 12 is a sectional view of a sensor element 101D according to a fifth embodiment. FIG. 13 is a sectional view taken along H-H in FIG. 12. The sensor element 101D is similar to the sensor element 101 according to the first embodiment except that the protective layer 84 includes a space 90D different from the space 90.

The space 90D includes an upper space 91D, a lower space 92D, a left space 93D, and a right space 94D. The upper space 91D is similar to the upper space 91 in the first embodiment except that a plurality of pillar portions P1 are formed to hold the upper space 91D in the direction perpendicular to the first surface 102a. Likewise, the other spaces 92D to 94D are also similar to the upper spaces 92 to 94 in the first embodiment, respectively, except that sets of plural pillar portions P2 to P4 are formed to hold the corresponding spaces, respectively, in the directions perpendicular to the corresponding second to fourth surfaces 102b to 102d.

Each of the pillar portions P2 is a part of the second protective layer 84b and has a rectangular pillar shape. Without being limited to the rectangular pillar shape, the pillar portion P2 may have the shape of a circular pillar, a triangular pillar, or a pentagonal or more polygonal pillar. As illustrated in FIG. 13, the pillar portions P2 are arranged with a tendency that a density of the pillar portions P2 gradually increases from the middle of a region of the second surface 102b in the back-forth direction, the region being covered with the protective layer 84, toward a position farther away from the middle when viewed from the direction perpendicular to the second surface 102b. More specifically, the pillar portions P2 are arranged with a tendency that the number of the pillar portions P2 per unit area gradually increases (namely, the pillar portions P2 are present more closely) toward a position farther away from the above-mentioned middle in the back-forth direction. Stated in another way, the pillar portions P2 are arranged with a tendency that the number of the pillar portions P2 per unit area gradually increases toward a front end or a rear end of a region of the second surface 102b, the region being covered with the protective layer 84.

Positional relations of the pillar portions P1, P3 and P4 relative to the corresponding first, third and fourth surfaces 102a, 102c and 102d, respectively, and shapes thereof are similar to the positional relation of the pillar portions P2 relative to the second surface 102b and the shape thereof. For example, the pillar portions P1 are arranged with a tendency that the number of the pillar portions P1 per unit area gradually increases from the middle of a region of the first surface 102a in the back-forth direction, the region being covered with the protective layer 84, toward a position farther away from the middle when viewed from the direction perpendicular to the first surface 102a. The pillar portions P3 are arranged with a tendency that the number of the pillar portions P3 per unit area gradually increases from the middle of a region of the third surface 102c in the back-forth direction, the region being covered with the protective layer 84, toward a position farther away from the middle when viewed from the direction perpendicular to the third surface 102c. The pillar portions P4 are arranged with a tendency that the number of the pillar portions P4 per unit area gradually increases from the middle of a region of the fourth surface 102d in the back-forth direction, the region being covered with the protective layer 84, toward a position farther away from the middle when viewed from the direction perpendicular to the fourth surface 102d. Moreover, in this embodiment, the pillar portions P1 and the pillar portions P2 are formed in shapes and layouts symmetrical in the up-down direction. The pillar portions P3 and the pillar portions P4 are formed in shapes and layouts symmetrical in the right-left direction.

Also in the sensor element 101D described above, as in the sensor element 101, the moisture resistance of the element body 102 is further improved with the presence of the spaces 91D to 94D. Moreover, looking at the lower space 92D, the second protective layer 84b includes one or more pillar portions P2 holding the lower space 92D in the direction perpendicular to the second surface 102b. Thus, since the pillar portions P2 hold the lower space 92D, the reduction in the strength of the second protective layer 84b can be suppressed. In addition, the second protective layer 84b includes the plurality of pillar portions P2, and these pillar portions P2 are arranged with a tendency that a density of the pillar portions P2 gradually increases from the middle of a region of the second surface 102b, the region being covered with the second protective layer 84b, toward a position farther away from the middle. Here, temperature in the middle of the region covered with the second protective layer 84b is comparatively more apt to become high, and temperature in a zone farther away from the middle (e.g., a zone nearer to an end of the second surface 102b) is comparatively less apt to become high. Therefore, by arranging the pillar portions P2 at a higher density in the zone where temperature is comparatively less apt to become high, reduction in the heat insulation effect of the lower space 92D attributable to the presence of the pillar portions P2 can be suppressed in the region where temperature is more apt to become high, while the reduction in the strength of the second protective layer 84b is suppressed by the pillar portions P2. It is hence possible to not only further improve the moisture resistance of the element body 102, but also further suppress the reduction in the strength of the second protective layer 84b. With respect to the other spaces 91D, 93D and 94D, similar advantageous effects can be obtained with similar constitutions to that described above.

Sixth Embodiment

Figure 14:
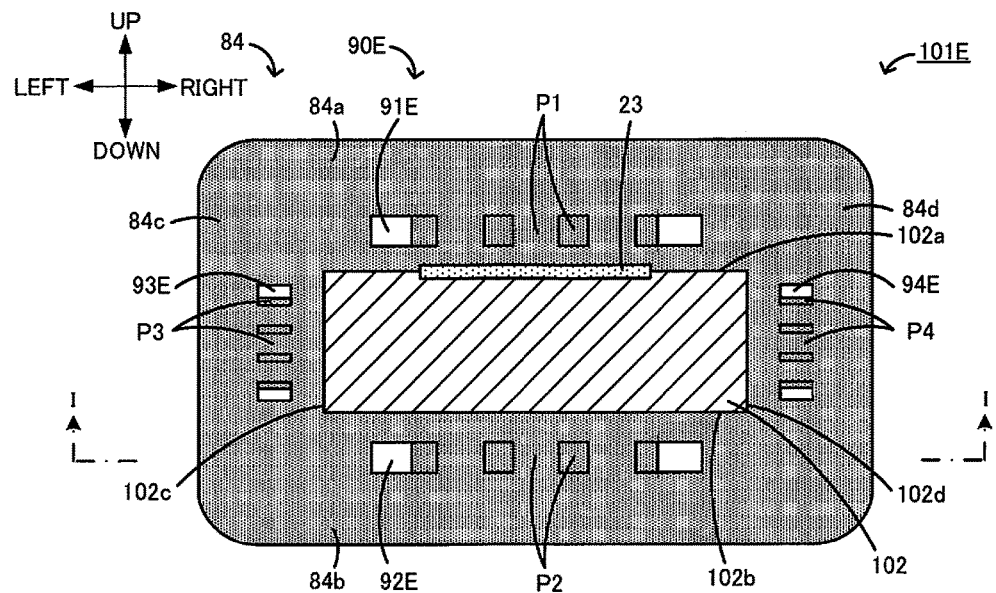
FIG. 14 is a sectional view of a sensor element 101E according to a sixth embodiment.
Figure 15:
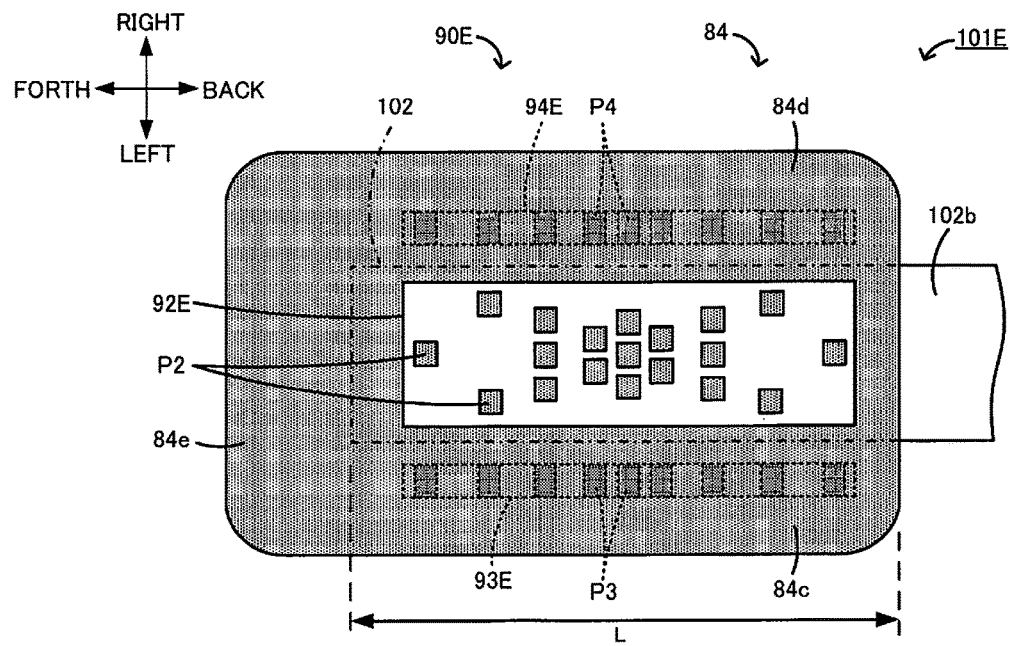
FIG. 15 is a sectional view taken along I-I in FIG. 14.

FIG. 14 is a sectional view of a sensor element 101E according to a sixth embodiment. FIG. 15 is a sectional view taken along I-I in FIG. 14. The sensor element 101E is similar to the sensor element 101D according to the fifth embodiment except that the protective layer 84 includes a space 90E different from the space 90D.

The space 90E includes an upper space 91E, a lower space 92E, a left space 93E, and a right space 94E. The spaces 91E to 94E are similar to the spaces 91D to 94D in the fifth embodiment, respectively, except that the layouts and the numbers of the pillar portions P1 to P4 for holding the spaces 91E to 94E are different.

As illustrated in FIG. 15, the pillar portions P2 are arranged with a tendency that a density of the pillar portions P2 gradually increases at a position nearer to the middle of a region of the second surface 102b in the back-forth direction, the region being covered with the protective layer 84, when viewed from the direction perpendicular to the second surface 102b. More specifically, the pillar portions P2 are arranged with a tendency that the number of the pillar portions P2 per unit area gradually increases (namely, the pillar portions P2 are present more closely) at a position nearer to the middle in the back-forth direction.

Positional relations of the pillar portions P1, P3 and P4 relative to the corresponding first, third and fourth surfaces 102a, 102c and 102d, respectively, and shapes thereof are similar to the positional relation of the pillar portions P2 relative to the second surface 102b and the shape thereof. For example, the pillar portions P1 are arranged with a tendency that the number of the pillar portions P1 per unit area gradually increases at a position nearer to the middle of a region of the first surface 102a in the back-forth direction, the region being covered with the protective layer 84, when viewed from the direction perpendicular to the first surface 102a. The pillar portions P3 are arranged with a tendency that the number of the pillar portions P3 per unit area gradually increases at a position nearer to the middle of a region of the third surface 102c in the back-forth direction, the region being covered with the protective layer 84, when viewed from the direction perpendicular to the third surface 102c. The pillar portions P4 are arranged with a tendency that the number of the pillar portions P4 per unit area gradually increases at a position nearer to the middle of a region of the fourth surface 102d in the back-forth direction, the region being covered with the protective layer 84, when viewed from the direction perpendicular to the fourth surface 102d. Moreover, in this embodiment, the pillar portions P1 and the pillar portions P2 are formed in shapes and layouts symmetrical in the up-down direction. The pillar portions P3 and the pillar portions P4 are formed in shapes and layouts symmetrical in the right-left direction.

Also in the sensor element 101E described above, as in the sensor element 101, the moisture resistance of the element body 102 is further improved with the presence of the spaces 91E to 94E. Moreover, since the pillar portions P2 hold the lower space 92 E, the reduction in the strength of the second protective layer 84b can be suppressed. With respect to the other spaces 91E, 93E and 94E, similar advantageous effects can be obtained with similar constitutions to that described above.

Seventh Embodiment

Figure 16:
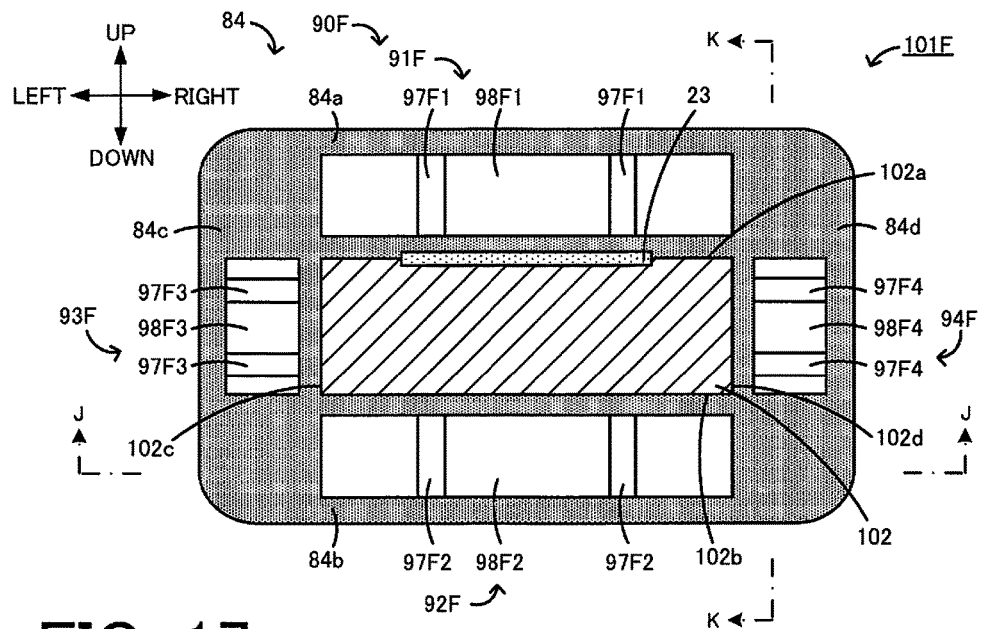
FIG. 16 is a sectional view of a sensor element 101F according to a seventh embodiment.
Figure 17:
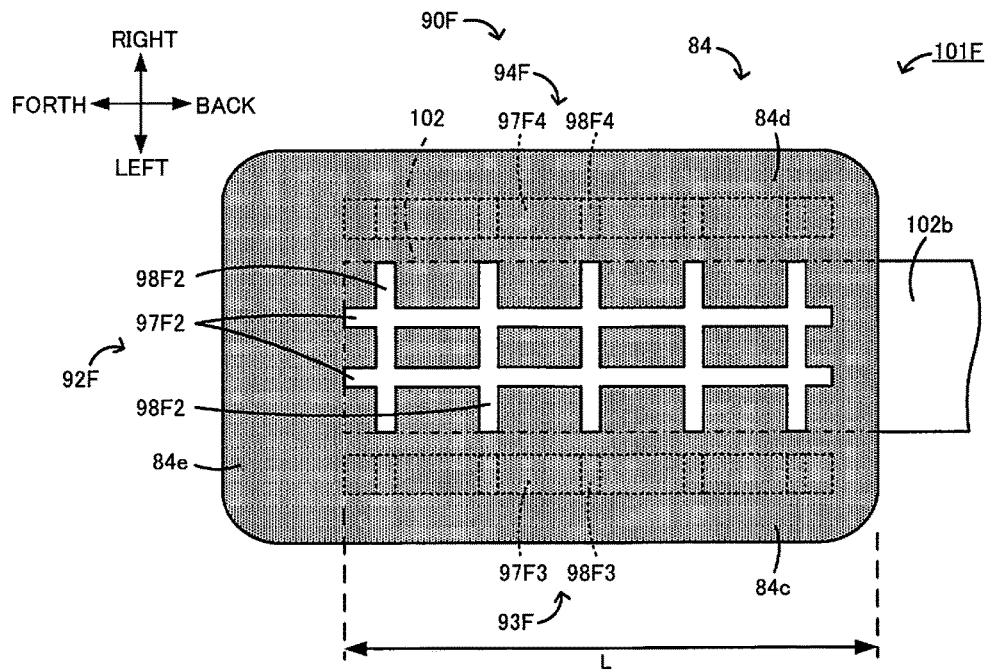
FIG. 17 is a sectional view taken along J-J in FIG. 16.
Figure 18:
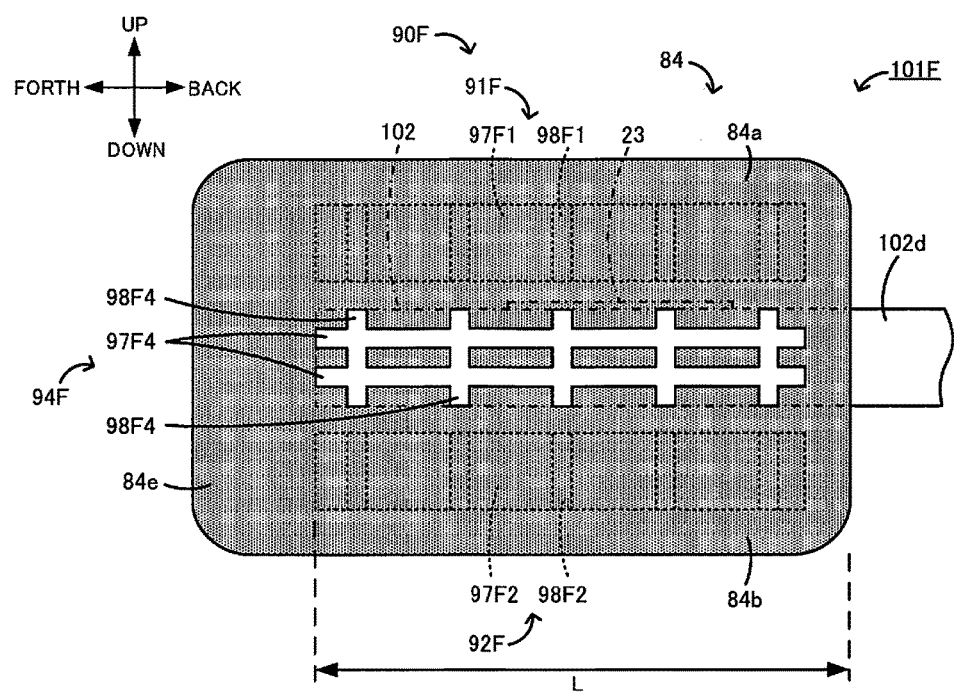
FIG. 18 is a sectional view taken along K-K in FIG. 16.

FIG. 16 is a sectional view of a sensor element 101F according to a seventh embodiment. FIG. 17 is a sectional view taken along J-J in FIG. 16. FIG. 18 is a sectional view taken along K-K in FIG. 16. The sensor element 101F is similar to the sensor element 101 according to the first embodiment except that the protective layer 84 includes a space 90F different from the space 90.

The space 90F includes an upper space 91F, a lower space 92F, a left space 93F, and a right space 94F. As illustrated in FIG. 17, the lower space 92F includes a plurality of first spaces 97F2 that are spaces each having a longitudinal direction aligned with the longitudinal direction of the second surface 102b (i.e., with the back-forth direction), and that are disposed side by side along the short-length direction of the second surface 102b (i.e., in the right-left direction). The lower space 92F further includes a plurality of second spaces 98F2 that are spaces each having a longitudinal direction aligned with the short-length direction of the second surface 102b and intersecting the first spaces 97F2, and that are disposed side by side along the longitudinal direction of the second surface 102b. In this embodiment, there are two first spaces 97F2, and five second spaces 98F2. The second spaces 98F2 are positioned at even intervals in the back-forth direction. The first spaces 97F2 and the second spaces 98F2 are present apart from the second surface 102b in a direction perpendicular to the second surface 102b.

The first spaces 97F2 and the second spaces 98F2 are each a space having a substantially rectangular parallelepiped shape. Each first space 97F2 has a slit-like shape and is formed such that one side of the first space 97F2 along the short-length direction of the second surface 102b (i.e., one side extending in the right-left direction) is shorter than the other two sides (i.e., sides extending in the up-down direction and the back-forth direction). Each second space 98F2 has a slit-like shape and is formed such that one side of the second space 98F2 along the longitudinal direction of the second surface 102b (i.e., one side extending in the back-forth direction) is shorter than the other two sides (i.e., sides extending in the up-down direction and the right-left direction).

The upper space 91F includes, similarly to the lower space 92F, a plurality of first spaces 97F1 and a plurality of second spaces 98F1. The left space 93F includes, similarly to the lower space 92F, a plurality of first spaces 97F3 and a plurality of second spaces 98F3. The right space 94F includes, similarly to the lower space 92F, a plurality of first spaces 97F4 and a plurality of second spaces 98F4.

Positional relations of the first spaces 97F1, 97F3 and 97F4 and the second spaces 98F1, 98F3 and 98F4 relative to the corresponding first, third and fourth surfaces 102a, 102c and 102d, respectively, and shapes thereof are similar to the positional relations of the first spaces 97F2 and the second spaces 98F2 relative to the second surface 102b and the shapes thereof. For example, the first spaces 97F1, 97F3 and 97F4 have longitudinal directions aligned respectively with the longitudinal directions of the corresponding first, third and fourth surfaces 102a, 102c and 102d (i.e., with the back-forth direction). The second spaces 98F1, 98F3 and 98F4 have longitudinal directions aligned respectively with the short-length directions of the corresponding first, third and fourth surfaces 102a, 102c and 102d. Moreover, the first spaces 97F1 intersect the second spaces 98F1, the first spaces 97F3 intersect the second spaces 98F3, and the first spaces 97F4 intersect the second spaces 98F4. In this embodiment, the upper space 91F and the lower space 92F are famed in shapes and layouts symmetrical in the up-down direction. The left space 93F and the right space 94F are formed in shapes and layouts symmetrical in the right-left direction.

Also in the sensor element 101F described above, as in the sensor element 101, the moisture resistance of the element body 102 is further improved with the presence of the spaces 91F to 94F. Moreover, the second protective layer 84b includes the plurality of first spaces 97F2 and the plurality of second spaces 98F2. Since the plural first spaces 97F2 being elongate in the longitudinal direction of the second surface 102b are present side by side along the short-length direction of the second surface 102b, stress generated, due to a difference in thermal expansion coefficient between the second protective layer 84b and the element body 102 when exposed to moisture, in the short-length direction of the second surface 102b and applied from the second protective layer 84b to the element body 102 can be reduced. Furthermore, since the plural second spaces 98F2 being elongate in the short-length direction of the second surface 102b are present side by side along the longitudinal direction of the second surface 102b, stress generated, due to the difference in thermal expansion coefficient between the second protective layer 84b and the element body 102 when exposed to moisture, in the longitudinal direction of the second surface 102b and applied from the second protective layer 84b to the element body 102 can be reduced. As a result, the element body 102 is less susceptible to cracking when exposed to moisture, and the moisture resistance of the element body 102 is further improved. With the presence of the spaces 91F, 93F and 94F, the first, third and fourth protective layers 84a, 84c and 84d can also provide similar advantageous effects with similar constitutions to that described above.

Eighth Embodiment

Figure 19:
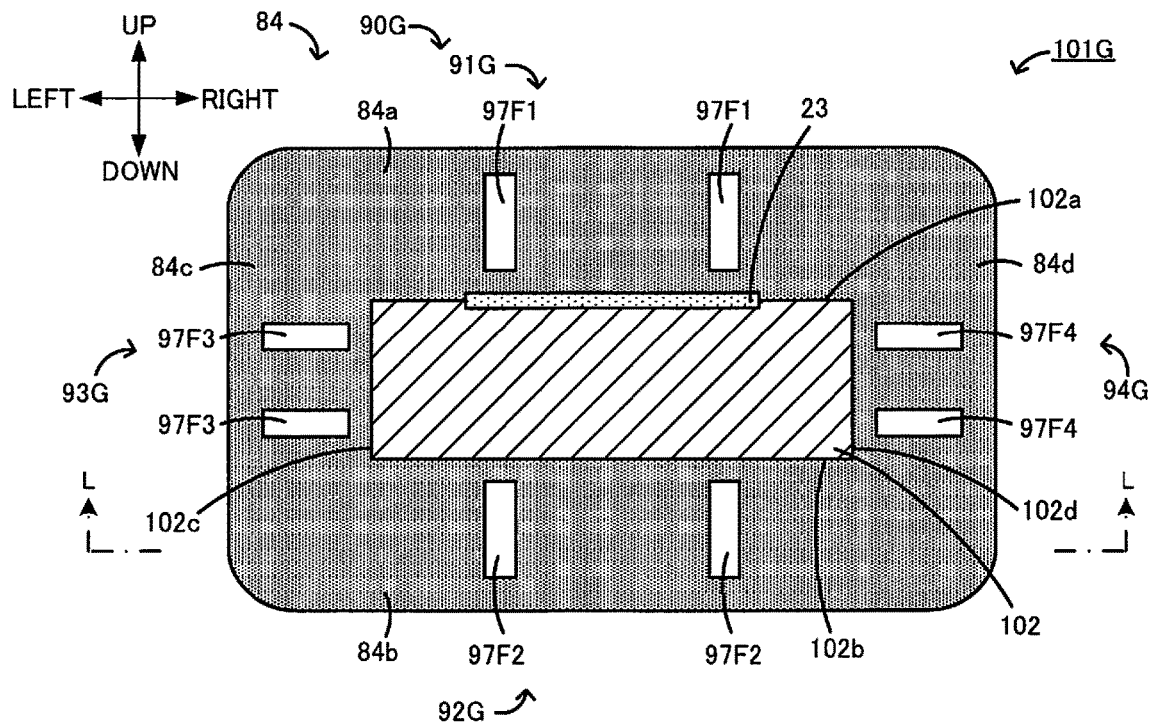
FIG. 19 is a sectional view of a sensor element 101G according to an eighth embodiment.
Figure 20:
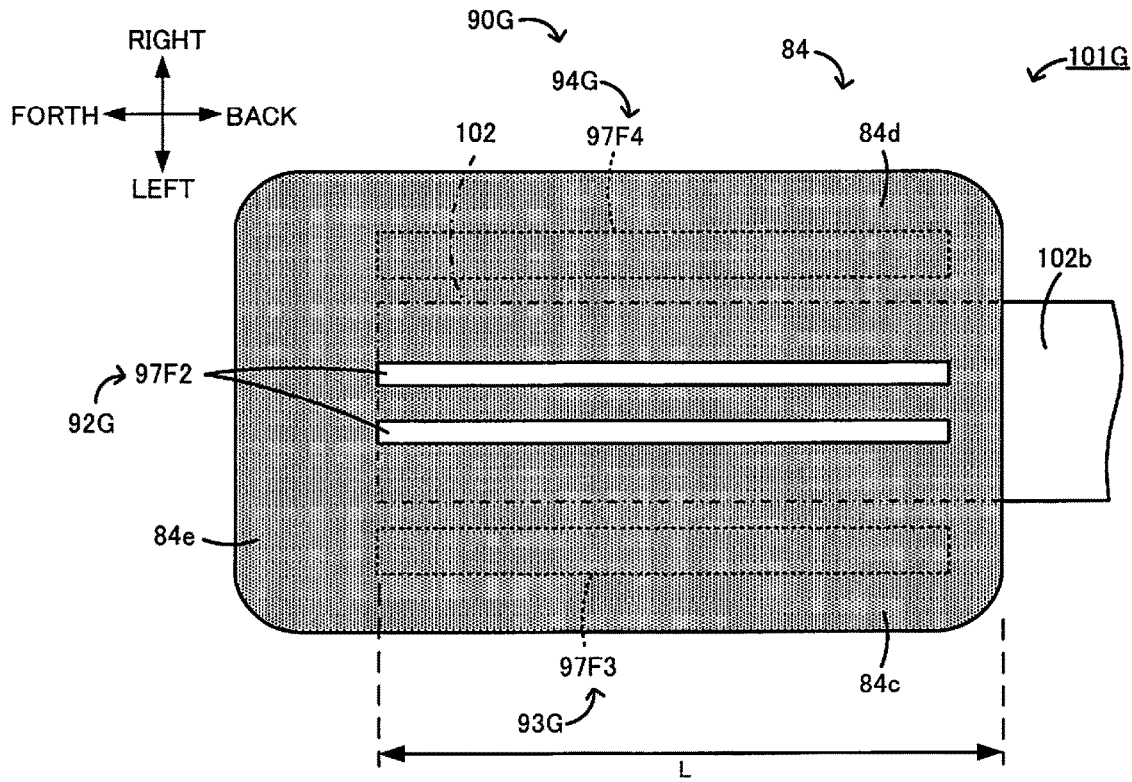
FIG. 20 is a sectional view taken along L-L in FIG. 19.

FIG. 19 is a sectional view of a sensor element 101G according to an eighth embodiment. FIG. 20 is a sectional view taken along L-L in FIG. 19. In the sensor element 101G, the protective layer 84 includes a space 90G. The space 90G includes an upper space 91G, a lower space 92G, a left space 93G, and a right space 94G. The upper space 91G includes the plurality of first spaces 97F1 and is similar to the upper space 91F in the seventh embodiment except for not including the second spaces 98F1. Likewise, the other spaces 92G to 94G include the plural first spaces 97F2 to 97F4, respectively, and they are similar to the spaces 92F to 94F in the seventh embodiment except for not including the second spaces 98F2 to 98F4, respectively.

Also in the sensor element 101G described above, as in the sensor element 101, the moisture resistance of the element body 102 is further improved with the presence of the spaces 91G to 94G. Moreover, since the second protective layer 84b includes the plurality of first spaces 97F2, stress generated, due to the difference in thermal expansion coefficient between the second protective layer 84b and the element body 102 when exposed to moisture, in the short-length direction of the second surface 102b and applied from the second protective layer 84b to the element body 102 can be reduced as in the seventh embodiment. As a result, the element body 102 is less susceptible to cracking when exposed to moisture, and the moisture resistance of the element body 102 is further improved. With the presence of the first spaces 97F1, 97F3 and 97F4, the first, third and fourth protective layers 84a, 84c and 84d can also provide similar advantageous effects with similar constitutions to that described above.

Ninth Embodiment

Figure 21:
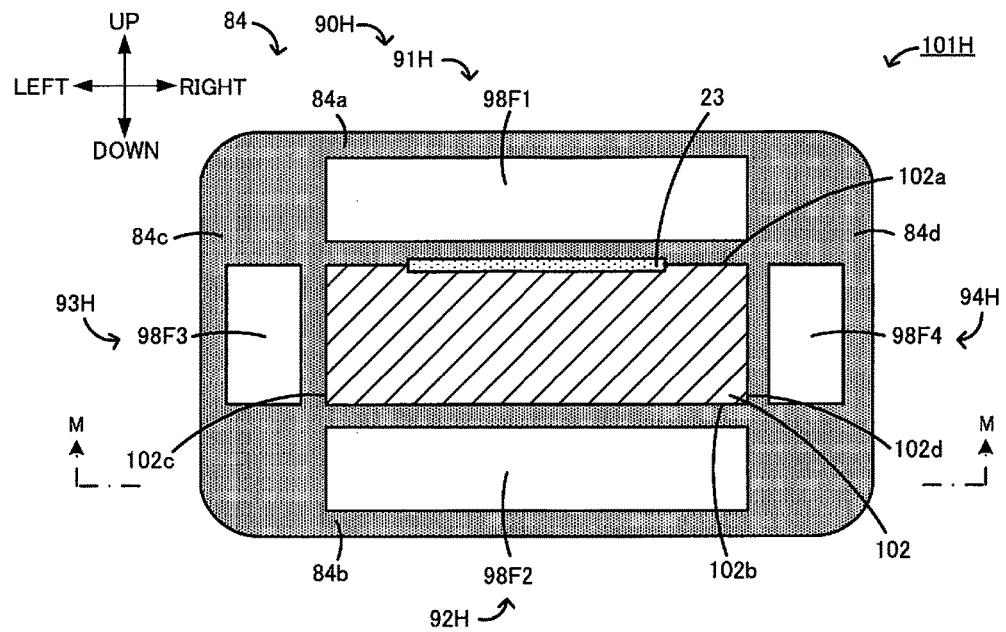
FIG. 21 is a sectional view of a sensor element 101H according to a ninth embodiment.
Figure 22:
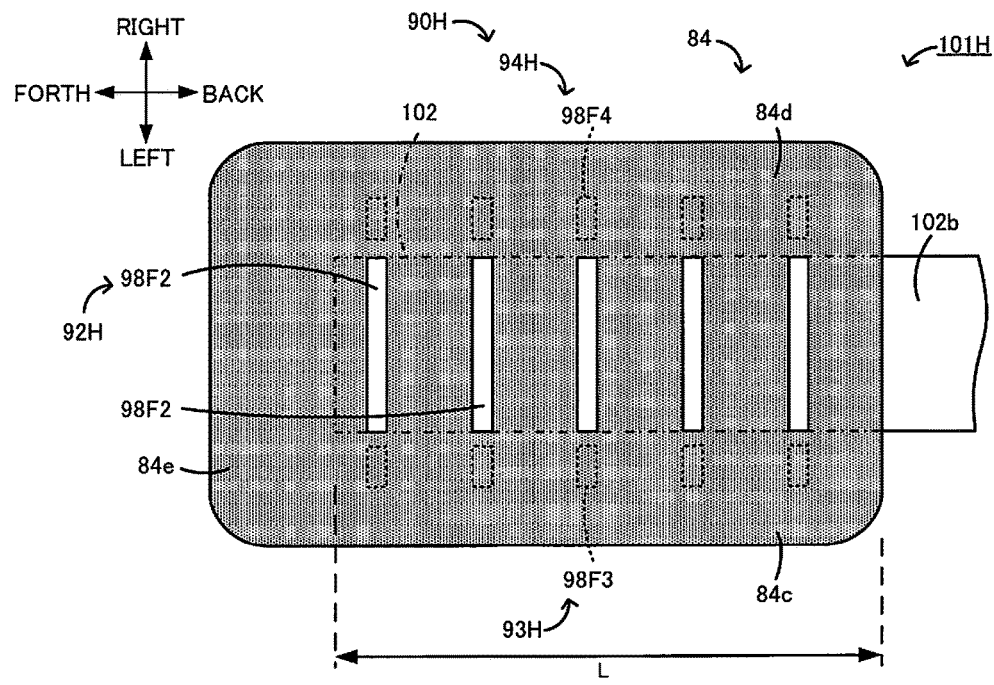
FIG. 22 is a sectional view taken along M-M in FIG. 21.

FIG. 21 is a sectional view of a sensor element 101H according to a ninth embodiment. FIG. 22 is a sectional view taken along M-M in FIG. 21. In the sensor element 101H, the protective layer 84 includes a space 90H. The space 90H includes an upper space 91H, a lower space 92H, a left space 93H, and a right space 94H. The upper space 91H includes the plurality of second spaces 98F1 and is similar to the upper space 91F in the seventh embodiment except for not including the first spaces 97F1. Likewise, the other spaces 92H to 94H include the plural second spaces 98F2 to 98F4, respectively, and they are similar to the spaces 92F to 94F in the seventh embodiment except for not including the first spaces 97F2 to 97F4, respectively.

Also in the sensor element 101H described above, as in the sensor element 101, the moisture resistance of the element body 102 is further improved with the presence of the spaces 91H to 94H. Moreover, since the second protective layer 84b includes the plurality of second spaces 98F2, stress generated, due to the difference in thermal expansion coefficient between the second protective layer 84b and the element body 102 when exposed to moisture, in the longitudinal direction of the second surface 102b and applied from the second protective layer 84b to the element body 102 can be reduced as in the seventh embodiment. As a result, the element body 102 is less susceptible to cracking when exposed to moisture, and the moisture resistance of the element body 102 is further improved. With the presence of the second spaces 98F1, 98F3 and 98F4, the first, third and fourth protective layers 84a, 84c and 84d can also provide similar advantageous effects with similar constitutions to that described above.

Tenth Embodiment

Figure 23:
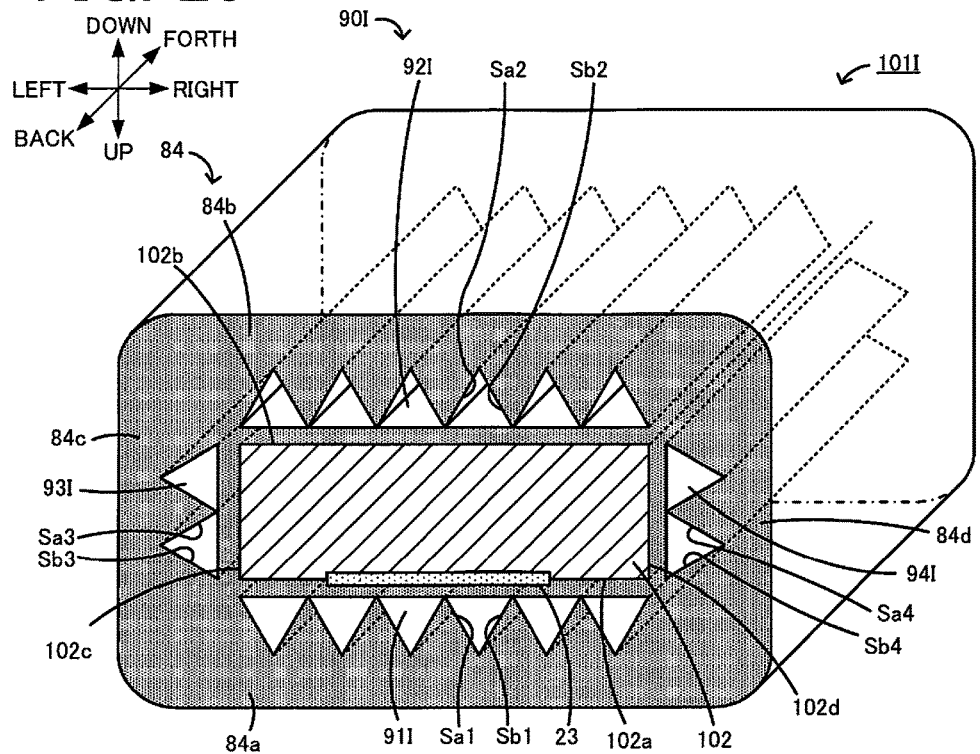
FIG. 23 is a sectional view of a sensor element 101I according to a tenth embodiment.
Figure 24:
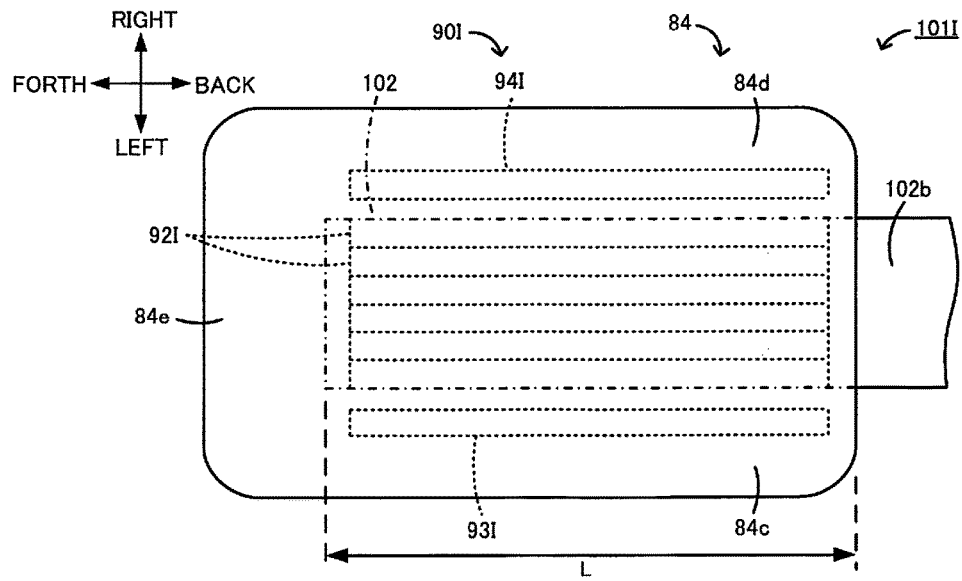
FIG. 24 is a bottom view of a part of the sensor element 101I near its front end.

FIG. 23 is a sectional view of a sensor element 101I according to a tenth embodiment. FIG. 24 is a bottom view of a part of the sensor element 101I near its front end. It is to be noted that FIG. 23 is the sectional view when looking at the sensor element 101I from the lower right side in the back. The sensor element 101I is similar to the sensor element 101 according to the first embodiment except that the protective layer 84 includes a space 90I different from the space 90.

The space 90I includes an upper space 91I, a lower space 92I, a left space 93I, and a right space 94I, which are each present plural. The lower spaces 92I are each a space that is present apart from the second surface 102b in a direction perpendicular to the second surface 102b. Each lower space 92I is a space having a substantially triangular pillar shape and having a longitudinal direction aligned with the longitudinal direction of the second surface 102b. The plural lower spaces 92I (six in this embodiment) are arranged side by side along the short-length direction of the second surface 102b. As illustrated in FIG. 23, each lower space 92I has a triangular shape in a cross-section perpendicular to the second surface 102b (i.e., in a cross-section taken along the up-down direction and the right-left direction). Thus, the lower space 92I has a shape providing a space that gradually narrows toward a position farther away from the second surface 102b (i.e., toward the lower side). Furthermore, the lower space 92I has inner surfaces Sa2 and Sb2 defining two sides of a triangle, which confront the second surface 102b when viewed in the cross-section perpendicular to the second surface 102b. The inner surfaces Sa2 and Sb2 are inclined in such directions that they come closer to each other at a position farther away from the second surface 102b, namely toward the lower side.

Like the lower space 92I, the other spaces 91I, 93I and 94I are also spaces that are present apart from the first, third and fourth surfaces 102a, 102c and 102d in the directions perpendicular to the first, third and fourth surfaces 102a, 102c and 102d, respectively. Moreover, the spaces 91I, 93I and 94I have inner surfaces Sa1, Sa3 and Sa4 and inner surfaces Sb1, Sb3 and Sb4, the paired inner surfaces defining two sides of a triangle, which confront the corresponding first, third and fourth surfaces 102a, 102c and 102d when viewed in the cross-sections perpendicular to the first, third and fourth surfaces, respectively. Positional relations of the spaces 91I, 93I and 94I relative to the corresponding first, third and fourth surfaces 102a, 102c and 102d, respectively, and shapes thereof are similar to the positional relation of the lower space 92I relative to the second surface 102b and the shape thereof. Moreover, there are two left spaces 93I and two right spaces 94I arranged side by side along the up-down direction. In this embodiment, the upper spaces 91I and the lower spaces 92I are formed in shapes and layouts symmetrical in the up-down direction. The left spaces 93I and the right spaces 94I are formed in shapes and layouts symmetrical in the right-left direction. In addition, four upper spaces 91I of the plural upper spaces 91I, the four being positioned in a central zone in the right-left direction, are positioned in a relation partly overlapping the outer pump electrode 23 such that the outer pump electrode 23 is included in the four upper spaces 91I positioned in the central zone in the right-left direction, when viewed from the direction perpendicular to the first surface 102a.

Also in the sensor element 101I described above, as in the sensor element 101, the moisture resistance of the element body 102 is further improved with the presence of the spaces 91I to 94I. Moreover, the lower space 92I has the shape providing the space that gradually narrows toward a position farther away from the second surface 102b. With the lower space 92I having the above-mentioned shape, the reduction in the strength of the second protective layer 84b can be suppressed in comparison with, for example, a rectangular parallelepiped space having an inner surface parallel to the second surface 102b, like the lower space 92 in FIG. 3.

Furthermore, the lower space 92I has at least two inner surfaces Sa2 and Sb2 inclined in such directions that they come closer to each other at a position farther away from the second surface 102b. With the lower space 92I having those inner surfaces Sa2 and Sb2, the reduction in the strength of the second protective layer 84b can be suppressed in comparison with, for example, a rectangular parallelepiped space having an inner surface parallel to the second surface 102b, like the lower space 92 in FIG. 3.

In addition, the second protective layer 84b includes the plurality of lower spaces 92I each of which has the longitudinal direction aligned with the longitudinal direction of the second surface 102b, and which are arranged side by side along the short-length direction of the second surface 102b. Therefore, stress generated, due to the difference in thermal expansion coefficient between the second protective layer 84b and the element body 102 when exposed to moisture, in the short-length direction of the second surface 102b and applied from the second protective layer 84b to the element body 102 can be reduced as in the sensor elements 101F and 101G. As a result, the element body 102 is less susceptible to cracking when exposed to moisture, and the moisture resistance of the element body 102 is further improved.

With the presence of the spaces 91I, 93I and 94I, the first, third and fourth protective layers 84a, 84c and 84d can also provide similar advantageous effects with similar constitutions to that of the second protective layer 84b.

Eleventh Embodiment

Figure 25:
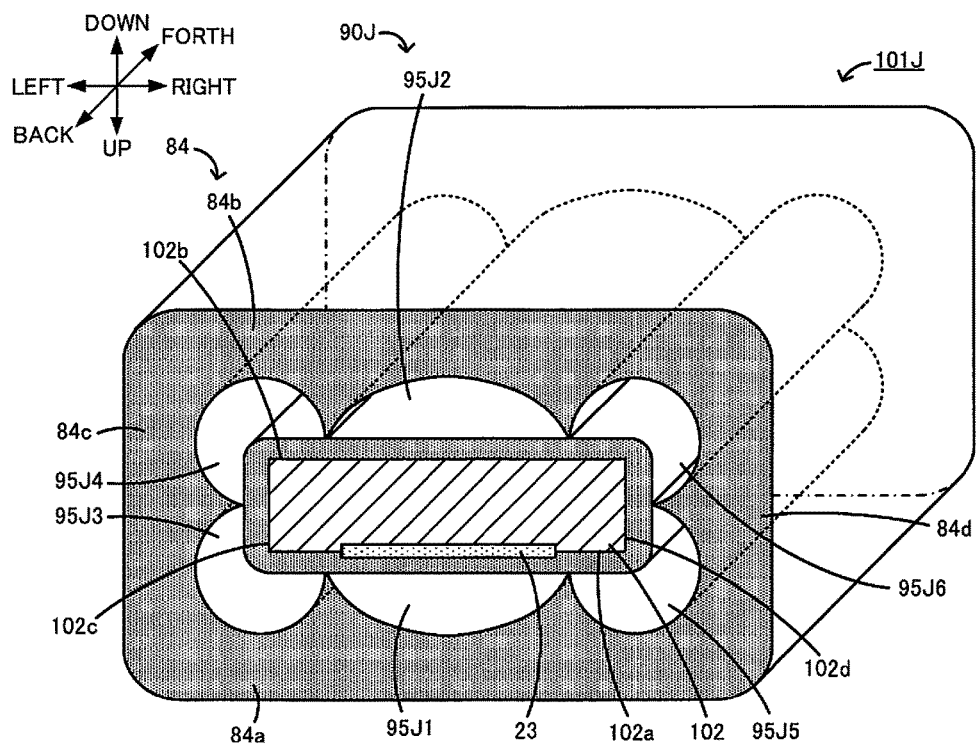
FIG. 25 is a sectional view of a sensor element 101J according to an eleventh embodiment.
Figure 26:
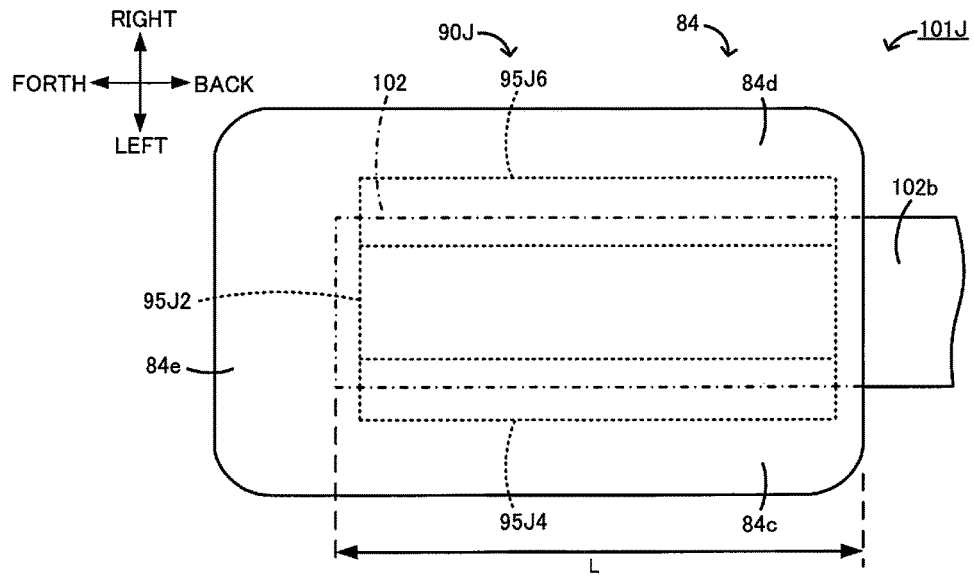
FIG. 26 is a bottom view of a part of the sensor element 101J near its front end.

FIG. 25 is a sectional view of a sensor element 101J according to an eleventh embodiment. FIG. 26 is a bottom view of the sensor element 101J near its front end. It is to be noted that FIG. 25 is the sectional view when looking at the sensor element 101J from the lower right side in the back. The sensor element 101J is similar to the sensor element 101 according to the first embodiment except that the protective layer 84 includes a space 90J different from the space 90. The space 90J includes spaces 95J1 to 95J6.

The space 95J2 is a space arranged on the lower side of the element body 102 and that is present apart from the second surface 102b in a direction perpendicular to the second surface 102b. The space 95J2 is a space having a semi-elliptic pillar shape, and an inner surface of the space 95J2 opposing the second surface 102b (i.e., an inner upward surface of the protective layer 84) is forted as a curved surface (corresponding to a part of an inner peripheral surface of a cylinder), which is obtained by bending a rectangle into a shape projecting toward the outside of the second protective layer 84b (i.e., downward). Thus, the space 95J2 has a semi-elliptic shape in a cross-section perpendicular to the second surface 102b (i.e., in a cross-section taken along the up-down direction and the right-left direction), and hence has a shape providing a space that gradually narrows toward a position farther away from the second surface 102b (i.e., toward the lower side). A longitudinal direction of the space 95J2 is aligned with the longitudinal direction of the second surface 102b.

The space 95J1 is a space arranged on the upper side of the element body 102, and is present apart from the first surface 102a in the direction perpendicular to the first surface 102a. The space 95J1 is a space having a semi-elliptic pillar shape, and an inner surface of the space 95J1 opposing the first surface 102a (i.e., an inner downward surface of the protective layer 84) is formed as a curved surface (corresponding to a part of an inner peripheral surface of a cylinder), which is obtained by bending a rectangle into a shape projecting toward the outside of the first protective layer 84a (i.e., upward). A longitudinal direction of the space 95J1 is aligned with the longitudinal direction of the first surface 102a. The outer pump electrode 23 is positioned to be entirely included in the space 95J1 when viewed from the direction perpendicular to the first surface 102a. The space 95J1 is symmetrical in shape and layout to the space 95J2 in the up-down direction.

The space 95J4 is a space arranged on the lower left side of the element body 102, and is present apart from the second surface 102b in the direction perpendicular to the second surface 102b and apart from the third surface 102c in the direction perpendicular to the third surface 102c. The space 95J4 has a shape obtained by cutting away a part of a circular pillar. An inner surface of the space 95J4 opposing the second surface 102b (i.e., an upward surface thereof) is formed as a curved surface (corresponding to a part of an inner peripheral surface of a cylinder), which is obtained by bending a rectangle into a shape projecting toward the outside of the second protective layer 84b (i.e., downward). Thus, the space 95J4 has a shape providing a space that gradually narrows toward a position farther away from the second surface 102b (i.e., toward the lower side). An inner surface of the space 95J4 opposing the third surface 102c (i.e., a rightward surface thereof) is formed as a curved surface (corresponding to a part of an inner peripheral surface of a cylinder), which is obtained by bending a rectangle into a shape projecting toward the outside of the third protective layer 84c (i.e., leftward). Thus, the space 95J4 has a shape providing a space that gradually narrows toward a position farther away from the third surface 102c (i.e., toward the left side). A longitudinal direction of the space 95J4 is aligned with the longitudinal direction of each of the second surface 102b and the third surface 102c.

The space 95J3 is a space arranged on the upper left side of the element body 102, and is present apart from the first surface 102a in the direction perpendicular to the first surface 102a and apart from the third surface 102c in the direction perpendicular to the third surface 102c. The space 95J3 is symmetrical in shape and layout to the space 95J4 in the up-down direction. The space 95J5 is a space arranged on the upper right side of the element body 102, and is present apart from the first surface 102a in the direction perpendicular to the first surface 102a and apart from the fourth surface 102d in the direction perpendicular to the fourth surface 102d. The space 95J5 is symmetrical in shape and layout to the space 95J3 in the right-left direction. The space 95J6 is a space arranged on the lower right side of the element body 102, and is present apart from the second surface 102b in the direction perpendicular to the second surface 102b and apart from the fourth surface 102d in the direction perpendicular to the fourth surface 102d. The space 95J6 is symmetrical in shape and layout to the space 95J4 in the right-left direction and to the space 95J5 in the up-down direction.

The spaces 95J1, 95J3 and 95J5 are arranged side by side along the short-length direction of the first surface 102a. The spaces 95J2, 95J4 and 95J6 are arranged side by side along the short-length direction of the second surface 102b. The spaces 95J3 and 95J4 are arranged side by side along the short-length direction of the third surface 102c. The spaces 95J5 and 95J6 are arranged side by side along the short-length direction of the fourth surface 102d.

Also in the sensor element 101J described above, as in the sensor element 101, the moisture resistance of the element body 102 is further improved with the presence of the spaces 95J1 to 95J6. Moreover, each of the spaces 95J2, 95J4 and 95J6 has the shape providing the space that gradually narrows toward a position farther away from the second surface 102b. In addition, the inner surfaces of the spaces 95J2, 95J4 and 95J6 opposing the second surface 102b are formed as the curved surfaces projecting outward. With those spaces each having the above-mentioned shape, the reduction in the strength of the second protective layer 84b can be suppressed in comparison with, for example, a rectangular parallelepiped space having an inner surface parallel to the second surface 102b, like the lower space 92 in FIG. 3.

Furthermore, the protective layer 84 includes the plurality of spaces each having the longitudinal direction aligned with the longitudinal direction of the second surface 102b, i.e., the spaces 95J2, 95J4 and 95J6, which are arranged side by side along the short-length direction of the second surface 102b. Therefore, stress generated, due to the difference in thermal expansion coefficient between the second protective layer 84b and the element body 102 when exposed to moisture, in the short-length direction of the second surface 102b and applied from the second protective layer 84b to the element body 102 can be reduced as in the sensor elements 101F and 101G. As a result, the element body 102 is less susceptible to cracking when exposed to moisture, and the moisture resistance of the element body 102 is further improved.

The spaces 95J1, 95J3 and 95J5 facing the first surface 102a, the spaces 95J3 and 95J4 facing the third surface 102c, and the spaces 95J5 and 95J6 facing the fourth surface 102d can also provide similar advantageous effects with similar constitutions of the spaces 95J2, 95J4 and 95J6 facing the second surface 102b.

Twelfth Embodiment

Figure 27:
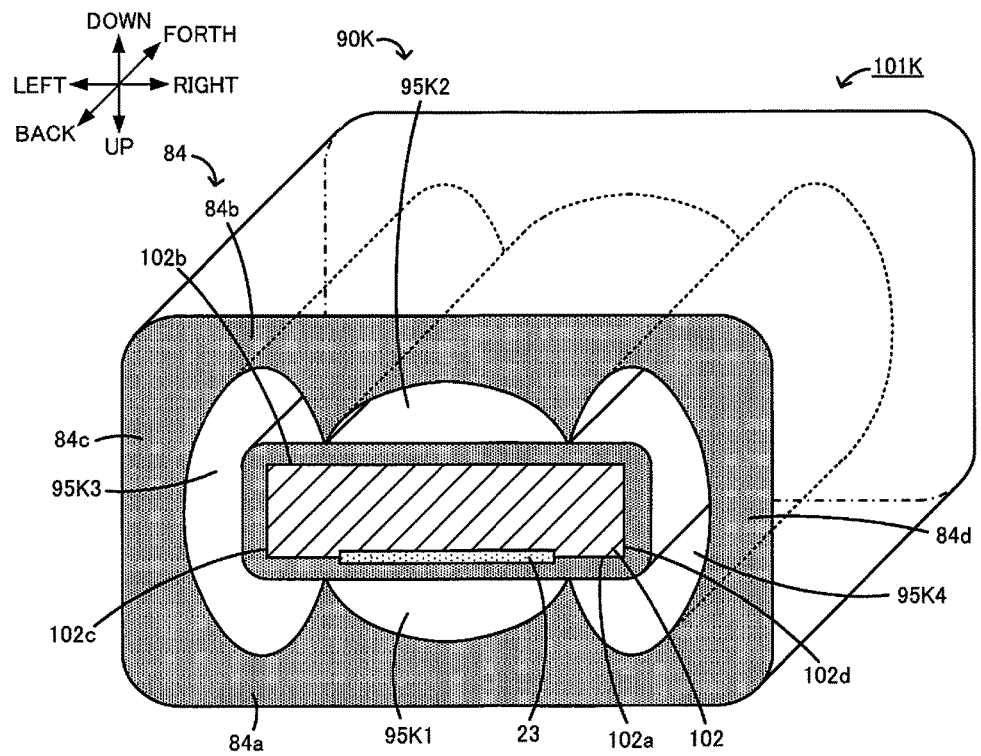
FIG. 27 is a sectional view of a sensor element 101K according to a twelfth embodiment.
Figure 28:
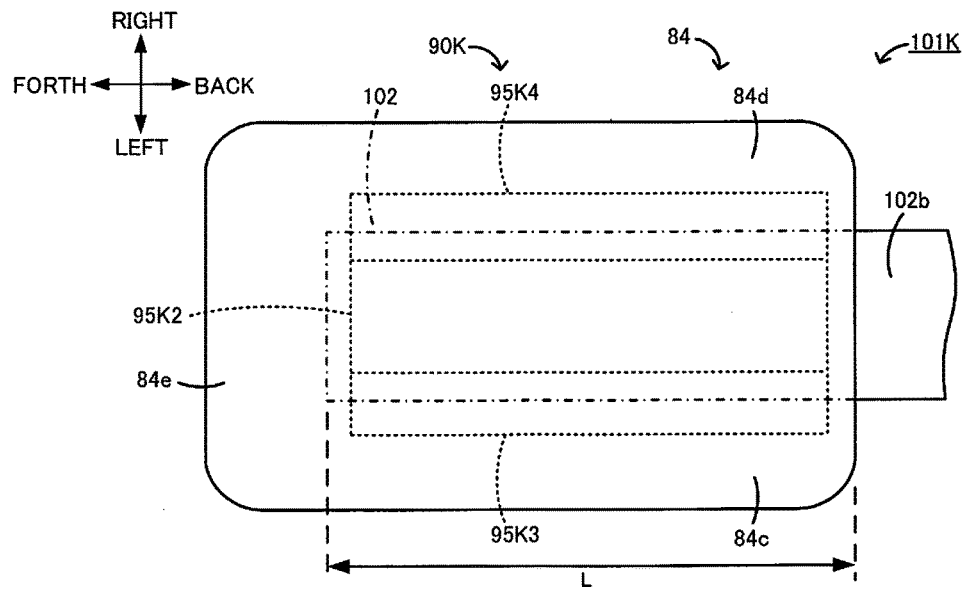
FIG. 28 is a bottom view of a part of the sensor element 101K near its front end.

FIG. 27 is a sectional view of a sensor element 101K according to a twelfth embodiment. FIG. 28 is a bottom view of the sensor element 101K near its front end. It is to be noted that FIG. 27 is the sectional view when looking at the sensor element 101K from the lower right side in the back. The sensor element 101K is similar to the sensor element 101 according to the first embodiment except that the protective layer 84 includes a space 90K different from the space 90. The space 90K includes spaces 95K1 to 95K4.

The spaces 95K1 and 95K2 are the same spaces as the spaces 95J1 and 95J2 in the sensor element 101J, respectively.

The space 95K3 is a space arranged to extend over the upper, lower and left sides of the element body 102. The space 95K3 is present apart from the first surface 102a in the direction perpendicular to the first surface 102a, apart from the second surface 102b in the direction perpendicular to the second surface 102b, and apart from the third surface 102c in the direction perpendicular to the third surface 102c. The space 95K3 has a shape obtained by cutting away a part of an elliptic pillar. An inner surface of the space 95K3 opposing the first surface 102a (i.e., a downward surface thereof) is formed as a curved surface (corresponding to a part of an inner peripheral surface of a cylinder), which is obtained by bending a rectangle into a shape projecting toward the outside of the first protective layer 84a (i.e., upward). Thus, the space 95K3 has a shape providing a space that gradually narrows toward a position farther away from the first surface 102a (i.e., toward the upper side). An inner surface of the space 95K3 opposing the second surface 102b (i.e., an upward surface thereof) is formed as a curved surface (corresponding to a part of an inner peripheral surface of a cylinder), which is obtained by bending a rectangle into a shape projecting toward the outside of the second protective layer 84b (i.e., downward). Thus, the space 95K3 has a shape providing a space that gradually narrows toward a position farther away from the second surface 102b (i.e., toward the lower side). Moreover, an inner surface of the space 95K3 opposing the third surface 102c (i.e., a rightward surface thereof) is formed as a curved surface (corresponding to a part of an inner peripheral surface of a cylinder), which is obtained by bending a rectangle into a shape projecting toward the outside of the third protective layer 84c (i.e., leftward). Thus, the space 95K3 has a shape providing a space that gradually narrows toward a position farther away from the third surface 102c (i.e., toward the left side). A longitudinal direction of the space 95K3 is aligned with the longitudinal direction of each of the first surface 102a, the second surface 102b, and the third surface 102c.

The space 95K4 is a space arranged to extend over the upper, lower and right sides of the element body 102. The space 95K4 is present apart from the first surface 102a in the direction perpendicular to the first surface 102a, apart from the second surface 102b in the direction perpendicular to the second surface 102b, and apart from the fourth surface 102d in the direction perpendicular to the fourth surface 102d. The space 95K4 is symmetrical in shape and layout to the space 95K3 in the right-left direction.

The spaces 95K1, 95K3 and 95K4 are arranged side by side along the short-length direction of the first surface 102a. The spaces 95K2, 95E3 and 95K4 are arranged side by side along the short-length direction of the second surface 102b.

Also in the sensor element 101K described above, as in the sensor element 101, the moisture resistance of the element body 102 is further improved with the presence of the spaces 95K1 to 95K4. Moreover, each of the spaces 95K2, 95K3 and 95K4 has the shape providing the space that gradually narrows toward a position farther away from the second surface 102b. In addition, the inner surfaces of the spaces 95K2, 95K3 and 95K4 opposing the second surface 102b are formed as the curved surfaces projecting outward. With those spaces each having the above-mentioned shape, the reduction in the strength of the second protective layer 84b can be suppressed in comparison with, for example, a rectangular parallelepiped space having an inner surface parallel to the second surface 102b, like the lower space 92 in FIG. 3. The spaces 95K1, 95K3 and 95K4 facing the first surface 102a, the space 95K3 facing the third surface 102c, and the space 95K4 facing the fourth surface 102d can also provide similar advantageous effects, i.e., the effects of suppressing the reduction in the strength of the first, third and fourth protective layers 84a, 84c and 84d with similar constitutions of the spaces 95K2, 95K3 and 95K4 facing the second surface 102b.

Furthermore, the protective layer 84 includes the plurality of spaces each having the longitudinal direction aligned with the longitudinal direction of the first surface 102a, i.e., the spaces 95K1, 95K3 and 95K4, which are arranged side by side along the short-length direction of the first surface 102a. Therefore, stress generated, due to the difference in thermal expansion coefficient between the first protective layer 84a and the element body 102 when exposed to moisture, in the short-length direction of the first surface 102a and applied from the first protective layer 84a to the element body 102 can be reduced as in the sensor elements 101F and 101G. As a result, the element body 102 is less susceptible to cracking when exposed to moisture, and the moisture resistance of the element body 102 is further improved. In addition, the protective layer 84 includes the plurality of spaces each having the longitudinal direction aligned with the longitudinal direction of the second surface 102b, i.e., the spaces 95K2, 95K3 and 95K4, which are arranged side by side along the short-length direction of the second surface 102b. Therefore, stress generated in the short-length direction of the second surface 102b and applied from the second protective layer 84b to the element body 102 can be reduced as in the sensor elements 101F and 101G. As a result, the element body 102 is less susceptible to cracking when exposed to moisture, and the moisture resistance of the element body 102 is further improved.

The spaces in the protective layer 84 in each of the second to twelfth embodiments described above can also be formed, as in the first embodiment, by employing a melt-disappearing material that disappears with burning.

It is needless to say that the present invention is not limited to the above-described embodiments, and that the present invention can be put into practice in various forms insofar as falling within the technical scope of the present invention.

While, in the first embodiment described above, the lower space 92 is positioned in an overlapping relation to the center of a region of the second surface 102b, the region being covered with the protective layer 84, when viewed from the direction perpendicular to the second surface 102b, the present invention is not limited to that case. For example, the lower space 92 may be positioned, when viewed from the direction perpendicular to the second surface 102b, in a relation overlapping the middle of a region of the second surface 102b in the back-forth direction, the region being covered with the protective layer 84, but not overlapping the middle of the relevant region in the right-left direction. As an alternative, the lower space 92 may be positioned in a relation overlapping the middle of the relevant region in the right-left direction, but not overlapping the middle of the relevant region in the back-forth direction, or it may be positioned in an overlapping relation to neither the middle of the relevant region in the right-left direction nor the middle of the relevant region in the back-forth direction.

In the first embodiment described above, assuming that a region of the second surface 102b where temperature is maximum in a state of the element body 102 being heated by the heater 72 to the temperature (e.g., about 800° C.) in an ordinary drive mode is called a maximum temperature region, the lower space 92 may be positioned in an overlapping relation to the maximum temperature region when viewed from the direction perpendicular to the second surface 102b. With such an arrangement, since the region of the second surface 102*b* where temperature is maximized during the use of the sensor element 101 can be heat-insulated by the lower space 92, the moisture resistance of the element body is further improved.

While, in the second embodiment described above, the spaces 91A to 94A are provided with the communication holes H1 to H4 in a one-to-one relation, respectively, the present invention is not limited to that case. One space may be provided with a plurality of communication holes. When the protective layer 84 includes a plurality of spaces, those spaces may include one or more spaces opened to the outside and one or more spaces not opened to the outside.

While, in the third embodiment described above, the inner spaces 95B2 and the outer spaces 96B2 are positioned at different heights in the up-down direction such that their positions do not overlap with each other when viewed from the direction perpendicular to the up-down direction, the present invention is not limited to that case, and the positions of both the spaces may partly overlap with each other when viewed from the direction perpendicular to the up-down direction. While the inner spaces 95B2 and the outer spaces 96B2 are arranged at positions deviated from each other in the back-forth direction, their positions in the back-forth direction may be the same. For example, the positions of the inner spaces 95B2 and the outer spaces 96B2 may be deviated only in the up-down direction, and may be the same in the back-forth direction and in the right-left direction. While the space 90B includes inner and outer spaces arrayed in two stages (e.g., the inner spaces 95B2 and the outer spaces 96B2), the present invention is not limited to that case, and the space 90B may include spaces arrayed in three or more stages. Among the plural inner spaces 95B2 and among the plural outer spaces 96B2, their heights may be different in the up-down direction. In the third embodiment, the protective layer 84 is not always required to include the outer spaces 96B1 to 96B4. Furthermore, in the third embodiment, the inner spaces 95B2 and the outer spaces 96B2 may be arranged with a tendency that a density of the spaces gradually increases toward a position nearer to the middle of a region of the second surface 102*b*, the region being covered with the protective layer 84, when viewed from the direction perpendicular to the second surface 102*b*. With such an arrangement, heat insulation can be enhanced in the zone where temperature is comparatively more apt to become high, and the moisture resistance of the element body 102 is further improved. The expression "a tendency that a density of the spaces gradually increases" includes a tendency that the number of spaces per unit area gradually increases, and a tendency that the space size gradually increases. The above-described modifications are similarly applicable to the fourth embodiment as well.

While, in the fifth and sixth embodiments described above, the density of the pillar portions P2 is changed by varying the number of the pillar portions P2 per unit area, the present invention is not limited to that case, and the density of the pillar portions P2 may be changed by varying the thicknesses of the pillar portions P2. The density of the pillar portions P2 is not always required to be specifically changed depending on locations.

While, in the fifth embodiment described above, the pillar portions P2 are arranged with a tendency that a density of the pillar portions P2 gradually increases from the middle of a region of the second surface 102*b* in the back-forth direction, the region being covered with the protective layer 84, toward a position farther away from the middle when viewed from the direction perpendicular to the second surface 102*b*, the present invention is not limited to that case. The pillar portions P2 may be arranged at a higher density at a position farther away from the middle in the right-left direction, or at a higher density at a position farther away from the middle in the back-forth direction and the middle in the right-left direction. Likewise, the pillar portions P2 in the sixth embodiment may also be arranged at a density that is changed not only in the back-forth direction, but also in the right-left direction.

While, in the seventh embodiment described above, one side of the first space 97F2 in the short-length direction of the second surface 102*b* is shorter than the other two sides, the present invention is not limited to that case. It is just required that the longitudinal direction of the first space 97F2 is aligned with the longitudinal direction of the second surface 102*b*. Similarly, while, in the seventh embodiment, one side of the second space 98F2 in the longitudinal direction of the second surface 102*b* is shorter than the other two sides, the present invention is not limited to that case. It is just required that the longitudinal direction of the second space 98F2 is aligned with the short-length direction of the second surface 102*b*.

While, in the eleventh embodiment described above, the space 95J4 is arranged to extend over the lower side and the left side of the element body 102, the present invention is not limited to that case. For example, the protective layer 84 may include, instead of the space 95J4, a space having a semi-elliptic pillar shape and formed on the lower side of the element body 102, and a space having a semi-elliptic pillar shape and formed on the left side of the element body 102. The Above point is similarly applied to the spaces 95J3, 95J5 and 95J6 and to the spaces 95K3 and 95K4 in the twelfth embodiment.

While, in the tenth to twelfth embodiments described above, the longitudinal direction of each of the spaces included in the protective layer 84 is aligned with the back-forth direction, the present invention is not limited to that case. The effect of suppressing the reduction in the strength of the second protective layer 84*b* can be obtained insofar as the space that is present apart from the second surface 102*b* in a direction perpendicular to the second surface 102*b* has a shape providing a space that gradually narrows toward a position farther away from the second surface 102*b*. For example, the lower space 92I in FIG. 23 may have a triangular pyramid shape. The space 95J2 in FIG. 25 may have a semi-spherical shape.

While, in the first to twelfth embodiments described above, the space(s) positioned on the upper side of the element body 102 and the space(s) positioned on the lower side thereof are symmetrical in the up-down direction and the space(s) positioned on the left side of the element body 102 and the space(s) positioned on the right side thereof are symmetrical in the right-left direction, the present invention is not limited to that case. Furthermore, while, in the first to twelfth embodiments described above, each of the first to fourth protective layers 84*a* to 84*d* includes the space(s), the present invention is not limited to that case. The protective layer 84 is just required to include one or more spaces that are present apart from the second surface 102*b* in a direction perpendicular to the second surface 102*b*. For example, in the first embodiment, the protective layer 84 is just required to include the lower space 92, and one or more of the upper space 91, the left space 93, and the right space 94 may be omitted. The fifth protective layer 84*e* may include one or more spaces similarly to the first to fourth protective layers 84*a* to 84*d*.

While, in the first to twelfth embodiments described above, the protective layer 84 includes the first to fifth protective layers 84*a* to 84*e*, the present invention is not limited to that case. The protective layer 84 is just required to include at least the second protective layer 84*b*. Moreover, the second protective layer 84*b* is just required to cover at least a part of the second surface 102*b*.

While, in the above embodiments, sizes of the spaces included in the protective layer 84 have not been described in particular, the spaces are just required to have sizes allowing the spaces to be distinguishable from pores in the protective layer 84. For example, the volume of one space may be 12500 µm$^3$ or more. Assuming a volume rate of the spaces to be denoted by (volume rate)=(total volume of the spaces in the protective layer 84)/(volume of the protective layer 84)×100, the volume rate may be 60% or less. The "volume of the protective layer 84" represents a value including the volume of the spaces in the protective layer 84.

Though not described in the above first to twelfth embodiments, the total volume of one or more spaces present under the second surface 102*b* is preferably 0.03 mm$^3$ or more. On that condition, the effect of improving the moisture resistance of the element body with the provision of the one or more spaces can be obtained reliably. For example, in the first to tenth embodiments described above, the total volume of each of the lower spaces 92 and 92A to 92I is preferably 0.03 mm$^3$ or more. In the eleventh embodiment, the total volume of the space 95J2, a portion of the space 95J4, the portion being positioned on the lower side of the second surface 102*b*, and a portion of the space 95J6, the portion being positioned on the lower side of the second surface 102*b*, is preferably 0.03 mm$^3$ or more. In the twelfth embodiment, the total volume of the space 95K2, a portion of the space 95K3, the portion being positioned on the lower side of the second surface 102*b*, and a portion of the space 95K4, the portion being positioned on the lower side of the second surface 102*b*, is preferably 0.03 mm$^3$ or more. Similarly, the total volume of one or more spaces present on the upper side of the first surface 102*a* is preferably 0.03 mm$^3$ or more. The total volume of one or more spaces present on the left side of the third surface 102*c* is preferably 0.015 mm$^3$ or more. The total volume of one or more spaces present on the right side of the fourth surface 102*d* is preferably 0.015 mm$^3$ or more. The expression "the lower side of the second surface 102*b*" implies a region containing, e.g., the lower left side and the lower right side of the second surface 102*b* without being limited to the side just under the second surface 102*b*. Similarly, the expression "the upper side of the first surface 102*a*" is not limited to the side just above the first surface 102*a*. The above point is similarly applied to "the left side of the third surface 102*c*" and "the right side of the fourth surface 102*d*".

Though not described in the above first to twelfth embodiments, when there is one or more spaces extending over two adjacent surfaces (i.e., surfaces having one common side), the total volume of the one or more spaces is preferably 0.002 mm$^3$ or more. With such a feature, the effect of improving the moisture resistance of the element body with the provision of the one or more spaces can be Obtained more reliably. For example, in the eleventh embodiment, the volume of the space 95J3 extending over the first surface 102*a* and the third surface 102*c* is preferably 0.002 mm$^3$ or more. Similarly, the volume of the space 95J4 extending over the second surface 102*b* and the third surface 102*c*, the volume of the space 95J5 extending over the first surface 102*a* and the fourth surface 102*d*, and the volume of the space 95J6 extending over the second surface 102*b* and the fourth surface 102*d* are each also preferably 0.002 mm$^3$ or more. The expression "the space extending over two adjacent surfaces" implies a space that is present in each of the directions perpendicular to those two surfaces. For example, the space 95J4 is present in the (downward) direction perpendicular to the second surface 102*b* and in the (leftward) direction perpendicular to the third surface 102*c*, and it is a space extending over the second surface 102*b* and the third surface 102*c*.

In the first to twelfth embodiments described above, the distance between the element body 102 and each of the spaces in the protective layer 84 is preferably 5 µm or more. On that condition, since the spaces in the protective layer 84 are all positioned apart from the element body 102, the reduction in the strength of the protective layer 84 attributable to the presence of the spaces can be suppressed. It is to be noted that the distance between the element body 102 and each of the spaces in the protective layer 84 is defined as a distance taken from one of the surfaces of the element body 102, the one surface being closest to the relevant space, in the direction perpendicular to the one surface. For example, the distance between the lower space 92 and the element body 102 in FIG. 3 is defined as a distance between the lower space 92 and the second surface 102*b* in the direction perpendicular to the second surface 102*b*.

While, in the first to twelfth embodiments described above, the spaces in the protective layer 84 are all apart from the element body 102, the protective layer 84 may further include one or more spaces not apart from the element body 102 (i.e., one or more spaces to which one or more surfaces of the element body 102 are exposed) in addition to the above-mentioned spaces. However, the strength of the protective layer 84 is more apt to reduce with the presence of the space to which the surface of the element body 102 is exposed than with the presence of the space that is present away from the element body 102. For that reason, the protective layer 84 preferably does not include the space to which the surface of the element body 102 is exposed.

The protective layer 84 may include an appropriate combination of two or more among not only the spaces constituting the spaces 90 and 90A to 90K in the first to twelfth embodiments described above, but also spaces modified from those spaces. That combination contains the case where the protective layer 84 includes different types of the spaces, and the case where the protective layer 84 includes spaces having the above-described features regarding the different types of shapes and layouts of the spaces.

For example, one or more of the above-described spaces except for the spaces in the second embodiment may be provided with an opening that is communicated with the outside of the protective layer 84. When the space is provided with the opening, a communication hole for communicating the space and the outside with each other like may be provided like the communication holes H1 to H4 in the second embodiment, or the space may be extended to the surface of the protective layer 84 to be directly opened to the outside. The opening associated with the space is preferably formed in such an appropriate size as being able not only to suppress moisture from directly entering the inside, but also to release heat within the space through the opening. An opening area may be set to 100 µm$^2$ to 1000 µm$^2$, for example.

As still another example, regarding the spaces in the embodiments other than the first embodiment, at least one of the spaces may be positioned in an overlapping relation to the middle of a region of the first surface 102*a*, the region being covered with the protective layer 84, or at least a part of the space may be positioned in an overlapping relation to the outer pump electrode 23 when viewed from the direction perpendicular to the first surface 102a.

The present application claims priority from Japanese Patent Application No. 2015-066703 filed on Mar. 27, 2015, and Japanese Patent Application No. 2016-049725 filed on Mar. 14, 2016, the entire contents of which are incorporated herein by reference.

What is claimed is:

1. A sensor element including:
an element body having an elongate rectangular parallelepiped shape and including solid electrolyte layers with oxygen ion conductivity,
an outer electrode disposed on a first surface that is one of surfaces of the element body, and
a protective layer covering at least a part of a second surface of the element body on a side opposite to the first surface and including one or more spaces that are present apart from the second surface in a direction perpendicular to the second surface,
the one or more spaces being provided within the protective layer such that a portion of the protective layer is provided between the one or more spaces and the second surface, and
the protective layer being made of a porous material comprising pores, and the one or more spaces each having a volume of 12500 $\mu m^3$ or more.

2. The sensor element according to claim 1, wherein at least one of the spaces is positioned in an overlapping relation to the middle of a region of the second surface, the region being covered with the protective layer, when viewed from a direction perpendicular to the second surface.

3. The sensor element according to claim 1, wherein at least one of the spaces is provided with an opening in communication with the outside of the protective layer.

4. The sensor element according to claim 1, wherein the one or more spaces includes a plurality of spaces, and
at least one of the plurality of spaces is present at a position deviated from at least another one space in the direction perpendicular to the second surface.

5. The sensor element according to claim 1, wherein the protective layer includes, for at least one of the spaces, one or more pillar portions that hold the space in the direction perpendicular to the second surface.

6. The sensor element according to claim 5,
wherein the one or more pillar portions includes a plurality of pillar portions, and
the pillar portions are arranged with a tendency that a density of the pillar portions gradually increases from the middle of a region of the second surface, the region being covered with the protective layer, toward a position farther away from the middle when viewed from the direction perpendicular to the second surface.

7. The sensor element according to claim 5,
wherein the one or more pillar portions includes a plurality of pillar portions, and
the pillar portions are arranged with a tendency that a density of the pillar portions gradually increases toward a position nearer to the middle of a region of the second surface, the region being covered with the protective layer, when viewed from the direction perpendicular to the second surface.

8. The sensor element according to claim 1, wherein the one or more spaces includes a plurality of spaces each having a longitudinal direction aligned with the longitudinal direction of the second surface and disposed side by side along the short-length direction of the second surface.

9. The sensor element according to claim 1, wherein the one or more spaces includes a plurality of spaces each having a longitudinal direction aligned with the short-length direction of the second surface and disposed side by side along the longitudinal direction of the second surface.

10. The sensor element according to claim 1, wherein the one or more spaces includes a plurality of first spaces each having a longitudinal direction aligned with the longitudinal direction of the second surface, and that are disposed side by side along the short-length direction of the second surface, and a plurality of second spaces each having a longitudinal direction aligned with the short-length direction of the second surface and intersecting the first spaces, and that are disposed side by side along the longitudinal direction of the second surface.

11. The sensor element according to claim 1, wherein at least one of the spaces has a shape with a tendency that the space gradually narrows toward a position farther away from the second surface.

12. The sensor element according to claim 1, wherein at least one of the spaces has at least two inner surfaces inclined in such directions that the inner surfaces come closer to each other toward a position farther away from the second surface.

13. The sensor element according to claim 1, wherein at least one of the spaces has an inner surface opposing the second surface and formed as a curved surface projecting outward.

14. A gas sensor including the sensor element according to claim 1.

15. A sensor element including:
an element body having an elongate rectangular parallelepiped shape and including solid electrolyte layers with oxygen ion conductivity,
an outer electrode disposed on a first surface that is one of surfaces of the element body, and
a protective layer covering at least a part of a second surface of the element body on a side opposite to the first surface and including one or more spaces that are present apart from the second surface in a direction perpendicular to the second surface,
the protective layer including, for at least one of the spaces, one or more pillar portions that hold the space in the direction perpendicular to the second surface.

16. A sensor element including:
an element body having an elongate rectangular parallelepiped shape and including solid electrolyte layers with oxygen ion conductivity,
an outer electrode disposed on a first surface that is one of surfaces of the element body, and
a protective layer covering at least a part of a second surface of the element body on a side opposite to the first surface and including one or more spaces that are present apart from the second surface in a direction perpendicular to the second surface,
the one or more spaces including a plurality of spaces each having a longitudinal direction aligned with the longitudinal direction of the second surface and disposed side by side along the short-length direction of the second surface.

17. A sensor element including:
an element body having an elongate rectangular parallelepiped shape and including solid electrolyte layers with oxygen ion conductivity,
an outer electrode disposed on a first surface that is one of surfaces of the element body, and a protective layer covering at least a part of a second surface of the element body on a side opposite to the first surface and including one or more spaces that are present apart from the second surface in a direction perpendicular to the second surface, the one or more spaces including a plurality of first spaces each having a longitudinal direction aligned with the longitudinal direction of the second surface, and that are disposed side by side along the short-length direction of the second surface, and a plurality of second spaces each having a longitudinal direction aligned with the short-length direction of the second surface and intersecting the first spaces, and that are disposed side by side along the longitudinal direction of the second surface.

* * * * *